United States Patent
Oosake et al.

(10) Patent No.: US 12,106,394 B2
(45) Date of Patent: *Oct. 1, 2024

(54) MEDICAL IMAGE PROCESSING APPARATUS, PROCESSOR DEVICE, ENDOSCOPE SYSTEM, MEDICAL IMAGE PROCESSING METHOD, AND PROGRAM

(71) Applicant: FUJIFILM Corporation, Tokyo (JP)

(72) Inventors: Masaaki Oosake, Kanagawa (JP); Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 556 days.

This patent is subject to a terminal disclaimer.

(21) Appl. No.: 17/379,036

(22) Filed: Jul. 19, 2021

(65) Prior Publication Data

US 2021/0342592 A1 Nov. 4, 2021

Related U.S. Application Data

(63) Continuation of application No. PCT/JP2019/041947, filed on Oct. 25, 2019.

(30) Foreign Application Priority Data

Feb. 26, 2019 (JP) .................. 2019-032944

(51) Int. Cl.
*G06T 11/00* (2006.01)
*A61B 1/00* (2006.01)
(Continued)

(52) U.S. Cl.
CPC ........ *G06T 11/00* (2013.01); *A61B 1/000094* (2022.02); *A61B 1/00045* (2013.01);
(Continued)

(58) Field of Classification Search
CPC ......... G06T 11/00; G06T 3/40; G06T 7/0012; G06T 11/60; G06T 2207/10068;
(Continued)

(56) References Cited

U.S. PATENT DOCUMENTS 5,734,915 A * 3/1998 Roewer ............... G06F 3/04845
715/202
2006/0165311 A1 * 7/2006 Watson ................. H04N 19/60
348/E17.005

(Continued)

FOREIGN PATENT DOCUMENTS

CN 107613839 A 1/2018
CN 108135457 A 6/2018
(Continued)

OTHER PUBLICATIONS

The extended European search report issued by the European Patent Office on Feb. 22, 2022, which corresponds to European Patent Application No. 17379036-1126 and is related to U.S. Appl. No. 17/379,036.

(Continued)

*Primary Examiner* — Michael R Neff
(74) *Attorney, Agent, or Firm* — Studebaker & Brackett PC

(57) ABSTRACT

A medical image processing apparatus includes a recognition unit that detects a region of interest from a medical image and classifies the region of interest, a display control unit that causes emphasis display of the region of interest and a classification for the region of interest to be displayed in a screen for displaying the observation target, and a change determining unit that determines at least any of whether to change a display style of the emphasis display or whether to change a display style of the classification. The display control unit changes the display style of the emphasis display in the case where it is determined to change the (Continued)

display style of the emphasis display and changes the display style of the classification in the case where it is determined to change the display style of the classification.

17 Claims, 12 Drawing Sheets

(51) Int. Cl.
  *G06F 3/14*     (2006.01)
  *G06F 18/24*    (2023.01)
  *G06T 3/40*     (2006.01)
  *G06T 7/00*     (2017.01)
  *G06T 11/60*    (2006.01)
  *G06V 10/25*    (2022.01)
  *G06V 10/82*    (2022.01)
  *G06V 20/20*    (2022.01)

(52) U.S. Cl.
  CPC .............. *G06F 3/14* (2013.01); *G06F 18/24* (2023.01); *G06T 3/40* (2013.01); *G06T 7/0012* (2013.01); *G06T 11/60* (2013.01); *G06V 10/25* (2022.01); *G06V 10/82* (2022.01); *G06V 20/20* (2022.01); *G06T 2207/10068* (2013.01); *G06T 2207/30004* (2013.01); *G06V 2201/03* (2022.01)

(58) Field of Classification Search
  CPC .......... G06T 2207/30004; G06V 10/25; G06V 20/20; G06V 10/82; G06V 2201/03; A61B 1/000094; A61B 1/00045; G06F 18/24; G06F 18/213; G06F 3/14
  USPC ........................................................ 382/128
  See application file for complete search history.

(56) References Cited

U.S. PATENT DOCUMENTS

| | | | |
|---|---|---|---|
| 2006/0274928 | A1 | 12/2006 | Collins et al. |
| 2007/0038086 | A1 | 2/2007 | Ohtsuka |
| 2007/0116347 | A1* | 5/2007 | Hong ............... G06T 7/143 382/173 |
| 2012/0220840 | A1 | 8/2012 | Morita et al. |
| 2015/0078615 | A1 | 3/2015 | Staples, II et al. |
| 2015/0187119 | A1 | 7/2015 | Masumoto |
| 2015/0339817 | A1 | 11/2015 | Kuriyama |
| 2016/0155227 | A1* | 6/2016 | Chae ............... A61B 8/5223 382/131 |
| 2016/0171708 | A1 | 6/2016 | Kim et al. |
| 2016/0314354 | A1* | 10/2016 | Teuton ............... G06V 20/695 |
| 2016/0331224 | A1 | 11/2016 | Uji et al. |
| 2018/0098690 | A1 | 4/2018 | Iwaki |
| 2018/0214005 | A1 | 8/2018 | Ebata |
| 2018/0242817 | A1 | 8/2018 | Imaizumi et al. |
| 2018/0249900 | A1 | 9/2018 | Imaizumi et al. |
| 2019/0282135 | A1 | 9/2019 | Ito et al. |
| 2020/0008653 | A1 | 1/2020 | Kamon |
| 2020/0035350 | A1* | 1/2020 | Sullivan ............... G06N 20/00 |
| 2020/0069160 | A1 | 3/2020 | Oosake |
| 2020/0126223 | A1 | 4/2020 | Kitamura et al. |
| 2020/0126224 | A1 | 4/2020 | Kamiyama et al. |
| 2020/0337537 | A1 | 10/2020 | Hirasawa et al. |
| 2020/0357118 | A1* | 11/2020 | Yao ............... G06N 3/045 |
| 2021/0366110 | A1* | 11/2021 | Oosake ............. A61B 1/00009 |

FOREIGN PATENT DOCUMENTS

| | | | |
|---|---|---|---|
| EP | 2149331 | A1 | 2/2010 |
| EP | 3357406 | A1 | 8/2018 |
| JP | 2005-124756 | A | 5/2005 |
| JP | 2007-209770 | A | 8/2007 |
| JP | 2009-105880 | A | 5/2009 |
| JP | 4451460 | B2 | 4/2010 |
| JP | 2012-005512 | A | 1/2012 |
| JP | 2014-054398 | A | 3/2014 |
| JP | 5658873 | B2 | 1/2015 |
| JP | 2015-097687 | A | 5/2015 |
| JP | 2015-167629 | A | 9/2015 |
| JP | 2016-174976 | A | 10/2016 |
| JP | 2016-214312 | A | 12/2016 |
| JP | 2017-060682 | A | 3/2017 |
| JP | 6176978 | B2 | 8/2017 |
| WO | 2017/057574 | A1 | 4/2017 |
| WO | 2017/073337 | A1 | 5/2017 |
| WO | 2017/073338 | A1 | 5/2017 |
| WO | 2017/081976 | A1 | 5/2017 |
| WO | 2018/105020 | A1 | 6/2018 |
| WO | 2018/179991 | A1 | 10/2018 |
| WO | 2018/198327 | A1 | 11/2018 |
| WO | 2018/221033 | A1 | 12/2018 |
| WO | 2018/235246 | A1 | 12/2018 |
| WO | 2019/003597 | A1 | 1/2019 |
| WO | 2019/088121 | A1 | 5/2019 |

OTHER PUBLICATIONS

International Search Report issued in PCT/JP2019/041947; mailed Dec. 24, 2019.
International Preliminary Report On Patentability and Written Opinion issued in PCT/JP2019/041947; issued Aug. 25, 2021.
Krizhevsky et al. ImageNet Classification with Deep Convolutional Neural Networks, Advances in Neural Information Processing Systems Conference, pp. 1-9 (2012).
Sermanet et al. "OverFeat: Integrated Recognition, Localization and Detection using Convolutional Networks", ICLR (International Conference on Learning Representations), p. 1-16, Feb. 24, 2014.
An Office Action mailed by China National Intellectual Property Administration on Dec. 13, 2023, which corresponds to Chinese Patent Application No. 201980092166.1 and is related to U.S. Appl. No. 17/379,036; with English language translation.
International Preliminary Report On Patentability and Written Opinion issued in PCT/JP2019/040362; issued Aug. 25, 2021.
International Search Report issued in PCT/JP2019/040362; mailed Dec. 17, 2019.
The extended European search report issued by the European Patent Office on Mar. 22, 2022, which corresponds to European Patent Application No. 19918612.3-1126.
An Office Action mailed by China National Intellectual Property Administration on Sep. 23, 2023, which corresponds to Chinese Patent Application No. 201980093038.9; with English language translation.
A Notice of Allowance mailed by the United States Patent and Trademark Office on Oct. 3, 2023, issued in U.S. Appl. No. 17/391,644 which is related to U.S. Appl. No. 17/379,036.

* cited by examiner

MEDICAL IMAGE PROCESSING APPARATUS, PROCESSOR DEVICE, ENDOSCOPE SYSTEM, MEDICAL IMAGE PROCESSING METHOD, AND PROGRAM

CROSS-REFERENCE TO RELATED APPLICATIONS

This application is a Continuation of PCT International Application No. PCT/JP2019/041947 filed on Oct. 25, 2019, which claims priority under 35 U.S.C § 119(a) to Japanese Patent Application No. 2019-032944 filed on Feb. 26, 2019. Each of the above application(s) is hereby expressly incorporated by reference, in its entirety, into the present application.

BACKGROUND OF THE INVENTION

Field of the Invention

The present invention relates to a medical image processing apparatus, a processor device, an endoscope system, a medical image processing method, and a program, and more particularly to screen display.

Description of the Related Art

A common endoscope system radiates illumination light from a tip of an insertion section of an endoscope, images an observation target by using an imaging element, and obtains image information of the observation target. An image obtained by imaging is displayed on a monitor. A user such as a doctor observes the image displayed on the monitor to perform examination.

In recent years, advanced automatic recognition using deep learning has become available. A. Krizhevsky, I. Sutskever, and G. Hinton, "ImageNet classification with deep convolutional neural networks.", NIPS (Neural Information Processing Systems conference), 2012 describes a technique relating to image recognition using deep learning. It is conceived that an endoscope system also automatically performs detection and classification of a lesion or the like by using a recognizer produced using deep learning. There is a technique called SSD (Single Shot multi box Detector) described in Pierre Sermanet, David Eigen, Xiang Zhang, Michael Mathieu, Rob Fergus, and Yann LeCun, "OverFeat: Integrated Recognition, Localization and Detection using Convolutional Networks", ICLR (International Conference on Learning Representations), 2014. This technique is known to enable detection and classification or the like to be collectively performed. Note that there may be cases where classification of a lesion or the like is referred to as differentiation.

JP6176978B describes an image processing apparatus. The image processing apparatus identifies a living-body mucous membrane, which is a subject to be emphasized, from an endoscopic image obtained by using an endoscope system, and performs emphasis processing on the identified living-body mucous membrane.

JP4451460B describes an endoscopic diagnosis assisting apparatus that automatically discriminates and classifies a type of a lesion on the basis of an endoscopic image obtained by using an endoscope system. The apparatus described in JP4451460B sets a ROI (Region Of Interest) in an endoscopic image, calculates a feature value for each ROI, and performs discrimination classification processing using the feature value. JP4451460B describes a neural network as an example of the discrimination classification processing.

JP5658873B describes an endoscope system configured to be capable of switching between observation under normal light and observation under special light. The system described in JP5658873B identifies a position of a lesion portion from a special-light image and processes a normal-light image on the basis of information of the identified position to increase the visual recognizability of the lesion portion. In JP5658873B, processing of superimposing a target color, processing of surrounding the periphery of the lesion portion by using a target color, and processing of combining the normal-light image and the special-light image of the lesion portion are described as examples of the processing performed on the normal-light image.

SUMMARY OF THE INVENTION

However, in the case of detecting a region of interest in a medical image such as an endoscopic image, displaying the region of interest in a screen, classifying the region of interest, and displaying the classification in the screen, notifications of the region of interest and the classification may hinder observation of an observation target performed by a doctor or the like.

The apparatus described in JP6176978B includes a switch with which a user gives an emphasis processing on/off instruction. In response to a user operating the switch, the apparatus sets, in an off state, the emphasis processing on a region of the living-body mucous membrane identified from an image obtained by imaging.

When the emphasis processing hinders observation of a living-body mucous membrane region, the user can sets the emphasis processing in the off state. However, if the emphasis processing is set in the off state, it becomes difficult to utilize diagnosis assist that uses the emphasis processing.

The apparatus described in JP4451460B opens a report display window and displays diagnosis assisting information including the determined classification result. Thus, when the report display window is open, the ROI in the endoscopic image cannot be observed.

The system described in JP5658873B can suppress an oversight of a lesion portion as a result of increasing the visual recognizability of the lesion portion. However, when a display style is inappropriate, display for increasing the visual recognizability of the lesion portion may hinder observation of the lesion portion.

The present invention is made in view of such circumstances, and an object thereof is to provide a medical image processing apparatus, a processor device, an endoscope system, a medical image processing method, and a program that suppress hindrance of observation of an observation target performed by a user or the like and enable the utilization of diagnosis assist when emphasis display and a classification for a region of interest are notified in a medical image.

In order to achieve the above object, the following aspects of the invention are provided.

A medical image processing apparatus according to a first aspect is a medical image processing apparatus including a recognition unit that detects a region of interest from an acquired medical image and classifies the region of interest; a display control unit that causes emphasis display for emphasizing the region of interest and a classification for the region of interest to be displayed in a screen identical to a screen for displaying an observation target included in the medical image; and a change determining unit that determines at least any of whether to change a display style of the emphasis display in a case where the emphasis display is displayed or whether to change a display style of the classification in a case where the classification is displayed, in which the display control unit makes a change to reduce a degree of emphasis of the emphasis display in a case where the change determining unit determines to change the display style of the emphasis display and makes a change to reduce visual recognizability of the classification in a case where the change determining unit determines to change the display style of the classification.

According to the first aspect, when a user observes the observation target, a situation may be suppressed in which at least any of the emphasis display or the classification hinders observation. In addition, the user may utilize at least any of the emphasis display or the classification when observing the observation target.

A style for visually emphasizing the region of interest may be used to emphasize the region of interest.

In a second aspect, the medical image processing apparatus according to the first aspect may further include a command signal acquisition unit that acquires a command signal transmitted when an operation section is operated, in which the change determining unit may determine to change the display style of the emphasis display in a case where the command signal acquisition unit acquires the command signal indicating that the display style of the emphasis display is to be changed and may determine to change the display style of the classification in a case where the command signal acquisition unit acquires the command signal indicating that the display style of the classification is to be changed.

According to the second aspect, when an operation section is operated, the display style of the region of interest and the display style of the classification for the region of interest may be changed.

In a third aspect, the medical image processing apparatus according to the first aspect or the second aspect may further include a classification performing signal acquisition unit that acquires a classification performing signal indicating whether the region of interest is being classified, in which the change determining unit may determine to change the display style of the emphasis display in a case where the classification performing signal acquisition unit acquires the classification performing signal indicating that the region of interest is being classified.

According to the third aspect, when the region of interest is being classified, the display style of the region of interest and the display style of the classification may be changed.

In a fourth aspect, the medical image processing apparatus according to any one of the first aspect to the third aspect may further include a treatment tool operation determining unit that determines whether a treatment tool is being operated, in which in a case where the treatment tool operation determining unit determines that the treatment tool is being operated, the change determining unit may determine to change the display style of the emphasis display, determine to change the display style of the classification, or determine to change the display styles of the emphasis display and the classification.

According to the fourth aspect, when the treatment tool is being operated, the display style of the region of interest and the display style of the classification may be changed.

In a fifth aspect, in the medical image processing apparatus according to any one of the first aspect to the fourth aspect, the recognition unit may include a plurality of downsizing processing units that perform processing for reducing a size of an input image in stages; and a feature map generation unit that generates a feature map from an output image of each of the plurality of downsizing processing units.

In a sixth aspect, in the medical image processing apparatus according to the fifth aspect, the downsizing processing units may include at least any of a pooling processing unit that performs pooling processing on the input image or a convolutional processing unit that performs convolutional processing on the input image.

According to the sixth aspect, a convolutional neural network may be used in detection of the region of interest and classification of the region of interest.

In a seventh aspect, in the medical image processing apparatus according to the fifth aspect or the sixth aspect, the recognition unit may include a region-of-interest recognition unit that performs at least any of detection of the region of interest or classification of the region of interest from a plurality of the feature maps generated by using the feature map generation unit.

According to the seventh aspect, the feature maps representing features of the input image may be used in at least any of detection of the region of interest or classification of the region of interest.

In an eighth aspect, in the medical image processing apparatus according to the seventh aspect, the region-of-interest recognition unit may perform detection of the region of interest and classification of the region of interest on the basis of an overlapping degree of the plurality of feature maps.

According to the eighth aspect, the region-of-interest detection accuracy and the region-of-interest classification accuracy may improve.

In a ninth aspect, in the medical image processing apparatus according to any one of the first aspect to the eighth aspect, the recognition unit may include a parameter storage unit that stores parameters obtained by collectively learning detection of a region of interest and classification of the region of interest for at least one image.

According to the ninth aspect, a region-of-interest detection process and a region-of-interest classification process may have a part in common.

In a tenth aspect, in the medical image processing apparatus according to any one of the first aspect to the ninth aspect, the display control unit may use a closed curve surrounding the region of interest as the emphasis display, and when changing the display style of the emphasis display, may change at least any of a color, a density, or a type of a line of the closed curve.

According to the tenth aspect, in the case where the closed curve is used as the emphasis display, the emphasis display can be weakened effectively.

In an eleventh aspect, in the medical image processing apparatus according to any one of the first aspect to the tenth aspect, when changing the display style of the emphasis display, the display control unit may move the emphasis display to a position where visual recognizability of the emphasis display is reduced.

According to the eleventh aspect, a situation may be suppressed in which the emphasis display hinders observation.

In a twelfth aspect, in the medical image processing apparatus according to any one of the first aspect to the eleventh aspect, the display control unit may use text information representing content of the classification as classification information representing the classification for the region of interest, and when changing the display style of the classification for the region of interest, may move the text information to a position where visual recognizability of the text information is reduced.

According to the twelfth aspect, a situation may be suppressed in which the text information representing content of the classification for the region of interest hinders observation In a thirteenth aspect, in the medical image processing apparatus according to the twelfth aspect, when changing the display style of the classification for the region of interest, the display control unit may move the text information to a position outside a display region of an image representing the observation target.

According to the thirteenth aspect, the text information is not superimposed on the image representing the observation target. Thus, a situation may be suppressed in which the text information hinders observation.

In a fourteenth aspect, in the medical image processing apparatus according to the thirteenth aspect, in a case where a plurality of the regions of interest are detected, the display control unit may move a plurality of pieces of the text information representing classifications for the plurality of regions of interest to positions outside the display region of the image representing the observation target while maintaining a positional relationship among the plurality of regions of interest.

According to the fourteenth aspect, the positional relationship among the plurality of regions of interest in the image representing the observation target may be grasped by using the positional relationship among the plurality of classifications.

In a fifteenth aspect, in the medical image processing apparatus according to any one of the twelfth aspect to the fourteenth aspect, when changing the display style of the classification for the region of interest, the display control unit may cause only an initial of a character string representing a meaning of the classification to be displayed as the text information.

According to the fifth aspect, the visual recognizability of the classification may be reduced and the content of the classification may be grasped.

A processor device according to a sixteenth aspect is a processor device including an endoscope control unit that controls an endoscope; a recognition unit that detects a region of interest from a medical image acquired by using the endoscope and classifies the region of interest; a display control unit that causes emphasis display for emphasizing the region of interest and a classification for the region of interest to be displayed in a screen identical to a screen for displaying an observation target included in the medical image; and a change determining unit that determines at least any of whether to change a display style of the emphasis display in a case where the emphasis display is displayed or whether to change a display style of the classification in a case where the classification is displayed, in which the display control unit makes a change to reduce a degree of emphasis of the emphasis display in a case where the change determining unit determines to change the display style of the emphasis display and makes a change to reduce visual recognizability of the classification in a case where the change determining unit determines to change the display style of the classification.

According to the sixteenth aspect, substantially the same advantages as those of the first aspect can be obtained.

The sixteenth aspect may be appropriately combined with any of features that are substantially the same as those specified in the second to fifteenth aspects. In such a case, a constituent element responsible for a process or function specified in the medical image processing apparatus can be grasped as a constituent element responsible for the corresponding process or function in the processor device.

An endoscope system according to a seventeenth aspect is an endoscope system including an endoscope; a processor device that controls the endoscope; and a medical image processing apparatus that performs processing on an endoscopic image acquired by using the endoscope, in which the medical image processing apparatus includes a recognition unit that detects a region of interest from an acquired medical image and classifies the region of interest; a display control unit that causes emphasis display for emphasizing the region of interest and a classification for the region of interest to be displayed in a screen identical to a screen for displaying an observation target included in the medical image; and a change determining unit that determines at least any of whether to change a display style of the emphasis display in a case where the emphasis display is displayed or whether to change a display style of the classification in a case where the classification is displayed, and in which the display control unit makes a change to reduce a degree of emphasis of the emphasis display in a case where the change determining unit determines to change the display style of the emphasis display and makes a change to reduce visual recognizability of the classification in a case where the change determining unit determines to change the display style of the classification.

According to the seventeenth aspect, substantially the same advantages as those of the first aspect can be obtained.

The seventeenth aspect may be appropriately combined with any of features that are substantially the same as those specified in the second to fifteenth aspects. In such a case, a constituent element responsible for a process or function specified in the medical image processing apparatus can be grasped as a constituent element responsible for the corresponding process or function in the endoscope system.

A medical image processing method according to an eighteenth aspect is a medical image processing method including a recognition step of detecting a region of interest from an acquired medical image and classifying the region of interest; a display step of causing emphasis display for emphasizing the region of interest and a classification for the region of interest to be displayed in a screen identical to a screen for displaying an observation target included in the medical image; and a change determining step of determining at least any of whether to change a display style of the emphasis display in a case where the emphasis display is displayed or whether to change a display style of the classification in a case where the classification is displayed, in which in the display step, a change is made to reduce a degree of emphasis of the emphasis display in a case where it is determined in the change determining step that the display style of the emphasis display is to be changed and a change is made to reduce visual recognizability of the classification in a case where it is determined in the change determining step that the display style of the classification is to be changed.

According to the eighteenth aspect, substantially the same advantages as those of the first aspect can be obtained.

The eighteenth aspect may be appropriately combined with any of features that are substantially the same as those specified in the second to fifteenth aspects. In such a case, a constituent element responsible for a process or function specified in the medical image processing apparatus can be grasped as a constituent element responsible for the corresponding process or function in the medical image processing method.

A program according to a nineteenth aspect is a program causing a computer to implement a recognition function that detects a region of interest from an acquired medical image and classifies the region of interest; a display function that causes emphasis display for emphasizing the region of interest and a classification for the region of interest to be displayed in a screen identical to a screen for displaying an observation target included in the medical image; and a change determining function that determines at least any of whether to change a display style of the emphasis display in a case where the emphasis display is displayed or whether to change a display style of the classification in a case where the classification is displayed, in which the display function makes a change to reduce a degree of emphasis of the emphasis display in a case where it is determined by using the change determining function that the display style of the emphasis display is to be changed and makes a change to reduce visual recognizability of the classification in a case where it is determined by using the change determining function that the display style of the classification is to be changed.

According to the nineteenth aspect, substantially the same advantages as those of the first aspect can be obtained.

The nineteenth aspect may be appropriately combined with any of features that are substantially the same as those specified in the second to fifteenth aspects. In such a case, a constituent element responsible for a process or function specified in the medical image processing apparatus can be grasped as a constituent element responsible for the corresponding process or function in the program.

According to the present invention, when a user observes an observation target, a situation may be suppressed in which at least any of emphasis display or a classification hinders observation. In addition, the user may utilize at least any of the emphasis display or the classification when observing the observation target.

DESCRIPTION OF THE PREFERRED EMBODIMENTS

Preferred embodiments of the present invention will be described in detail below with reference to the accompanying drawings. The same constituent elements are denoted by the same reference signs herein, and redundant description will be appropriately omitted.

Overall Configuration of Endoscope System

Figure 1:
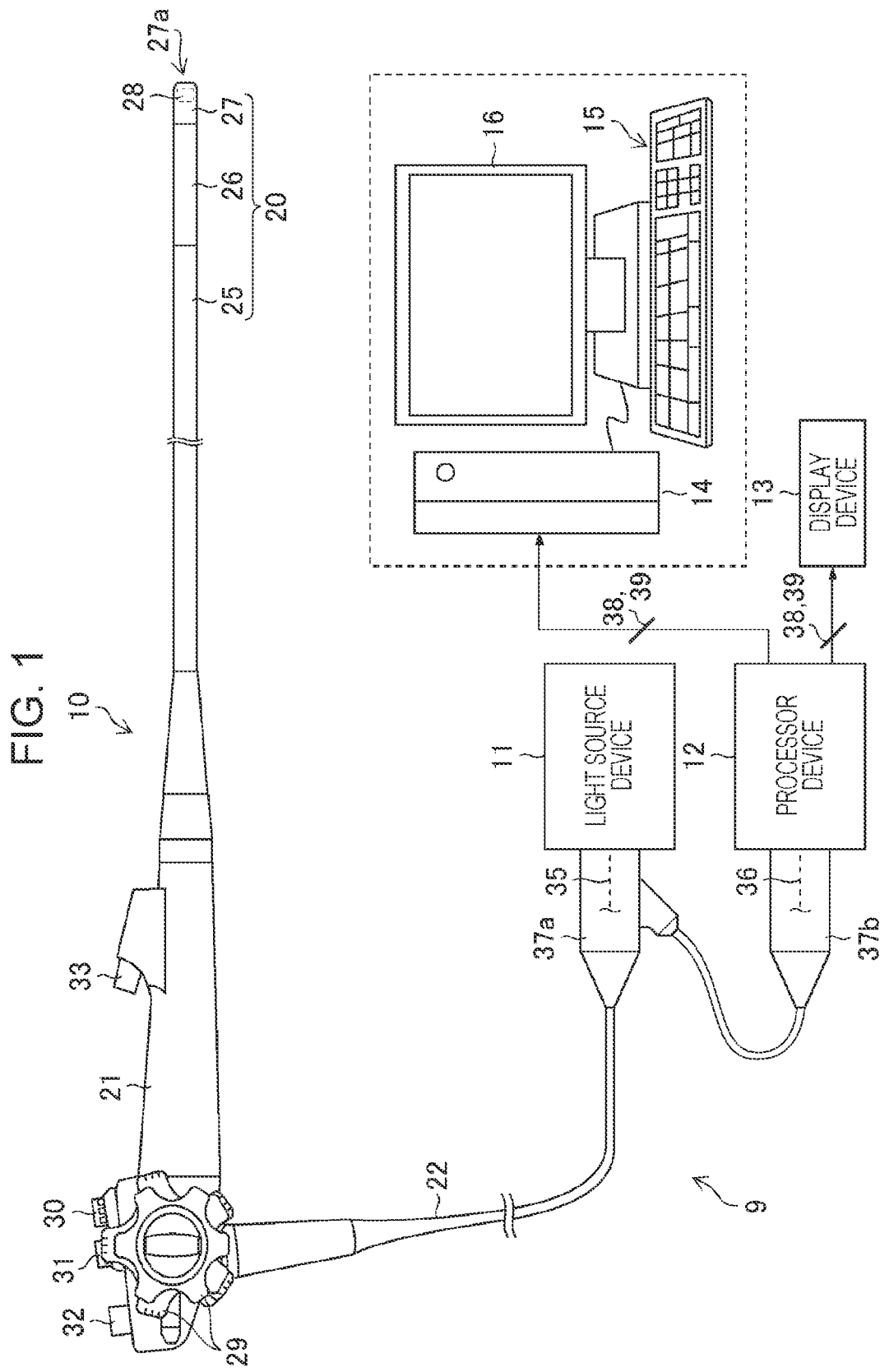
FIG. 1 is an overall configuration diagram of an endoscope system including a medical image processing apparatus according to an embodiment.

FIG. 1 is an overall configuration diagram of an endoscope system including a medical image processing apparatus according to an embodiment. An endoscope system 9 illustrated in FIG. 1 includes an endoscope 10, a light source device 11, a processor device 12, a display device 13, a medical image processing apparatus 14, an input device 15, and a monitor device 16.

The endoscope 10 illustrated in FIG. 1 is an electronic endoscope and is also a flexible endoscope. The endoscope 10 includes an insertion section 20, an operation section 21, and a universal cord 22. The insertion section 20 is inserted into a subject. The entire insertion section 20 is formed to have an elongated shape with a small diameter.

The insertion section 20 includes a soft part 25, a bending part 26, and a tip part 27. The soft part 25, the bending part 26, and the tip part 27 are coupled to each other to constitute the insertion section 20. The soft part 25 has flexibility sequentially from a proximal end side toward a tip side of the insertion section 20. The bending part 26 has a structure that is bendable when the operation section 21 is operated. The tip part 27 includes an imaging optical system (not illustrated), an imaging element 28, and so on.

A CMOS imaging element or a CCD imaging element is used as the imaging element 28. Note that CMOS is an abbreviation for Complementary Metal Oxide Semiconductor. CCD is an abbreviation for Charge Coupled Device.

An observation window (not illustrated) is provided at a tip surface 27a of the tip part 27. The observation window is an opening formed at the tip surface 27a of the tip part 27. A cover (not illustrated) is attached to the observation window. The imaging optical system (not illustrated) is provided behind the observation window. Image light of a site to be observed is incident onto an imaging surface of the imaging element 28 through the observation window, the imaging optical system, and so on. The imaging element 28 images the image light of the site to be observed incident onto the imaging surface of the imaging element 28 and outputs an imaging signal. The term "imaging" used herein includes the meaning of converting light reflected off from a site to be observed into an electric signal.

The operation section 21 is coupled to the proximal end side of the insertion section 20. The operation section 21 includes various operating members to be operated by a technician. Specifically, the operation section 21 includes two types of bending operation knobs 29. The bending operation knobs 29 are used when an operation of bending the bending part 26 is performed. Note that the technician may include a doctor, an operator, an observer, a user, and the like.

The operation section 21 includes an air/water supply button 30 and a suction button 31. The air/water supply button 30 is used when the technician performs an air/water supply operation. The suction button 31 is used when the technician performs a suction operation.

The operation section 21 includes a still image capturing instruction part 32 and a treatment tool introduction port 33. The still image capturing instruction part 32 includes a button that is operated by the technician when a still image of the site to be observed is captured.

The treatment tool introduction port 33 is an opening through which a treatment tool is inserted into a treatment tool insertion path that is inserted inside the insertion section 20. Note that illustration of the treatment tool insertion path and the treatment tool is omitted.

The universal cord 22 is a connection cord that connects the endoscope 10 to the light source device 11. The universal cord 22 includes therein a light guide 35, a signal cable 36, and a fluid tube (not illustrated), which are inserted inside the insertion section 20.

In addition, a tip part of the universal cord 22 includes a connector 37a to be connected to the light source device 11 and a connector 37b branching from the connector 37a and to be connected to the processor device 12.

When the connector 37a is connected to the light source device 11, the light guide 35 and the fluid tube (not illustrated) are inserted into the light source device 11. Consequently, necessary illumination light, a liquid such as water, and a gas such as air are supplied to the endoscope 10 from the light source device 11 through the light guide 35 and the fluid tube (not illustrated).

As a result, the illumination light is radiated from an illumination window (not illustrated) of the tip surface 27a of the tip part 27 toward the site to be observed. In addition, in response to an operation of pressing the air/water supply button 30, a gas or water is ejected from an air/water supply nozzle (not illustrated) of the tip surface 27a of the tip part 27 toward the observation window (not illustrated) of the tip surface 27a. Note that the site to be observed may be referred to as an observation target, an examination target, or the like in some cases.

When the connector 37b is connected to the processor device 12, the signal cable 36 and the processor device 12 are electrically connected to each other. Consequently, an imaging signal of the site to be observed is output from the imaging element 28 of the endoscope 10 to the processor device 12 through the signal cable 36. Also, a control signal is output from the processor device 12 to the endoscope 10 through the signal cable 36.

In the present embodiment, the flexible endoscope is described as an example of the endoscope 10. However, various types of electronic endoscopes capable of capturing a moving image of a site to be observed, such as a rigid endoscope, may be used as the endoscope 10.

The light source device 11 supplies illumination light to the light guide 35 of the endoscope 10 through the connector 37a. White light or light in a specific wavelength range is usable as the illumination light. As the illumination light, white light and light in a specific wavelength range may be used in combination. The light source device 11 is configured to be capable of appropriately selecting, as the illumination light, light in a wavelength range corresponding to an observation purpose.

The white light may be light in a white wavelength range or light in a plurality of wavelength ranges. The specific wavelength range is a range narrower than the white wavelength range. As the light in the specific wavelength range, light in a single wavelength range may be used, or light in a plurality of wavelength ranges may be used. Light in the specific wavelength range may be referred to as special light.

The processor device 12 transmits a command signal to the endoscope 10 through the connector 37b and the signal cable 36 to control operation of the endoscope 10. The processor device 12 also acquires an imaging signal from the imaging element 28 of the endoscope 10 through the connector 37b and the signal cable 36. That is, the processor device 12 uses a predetermined frame rate to acquire an imaging signal output from the endoscope 10.

Figure 3:
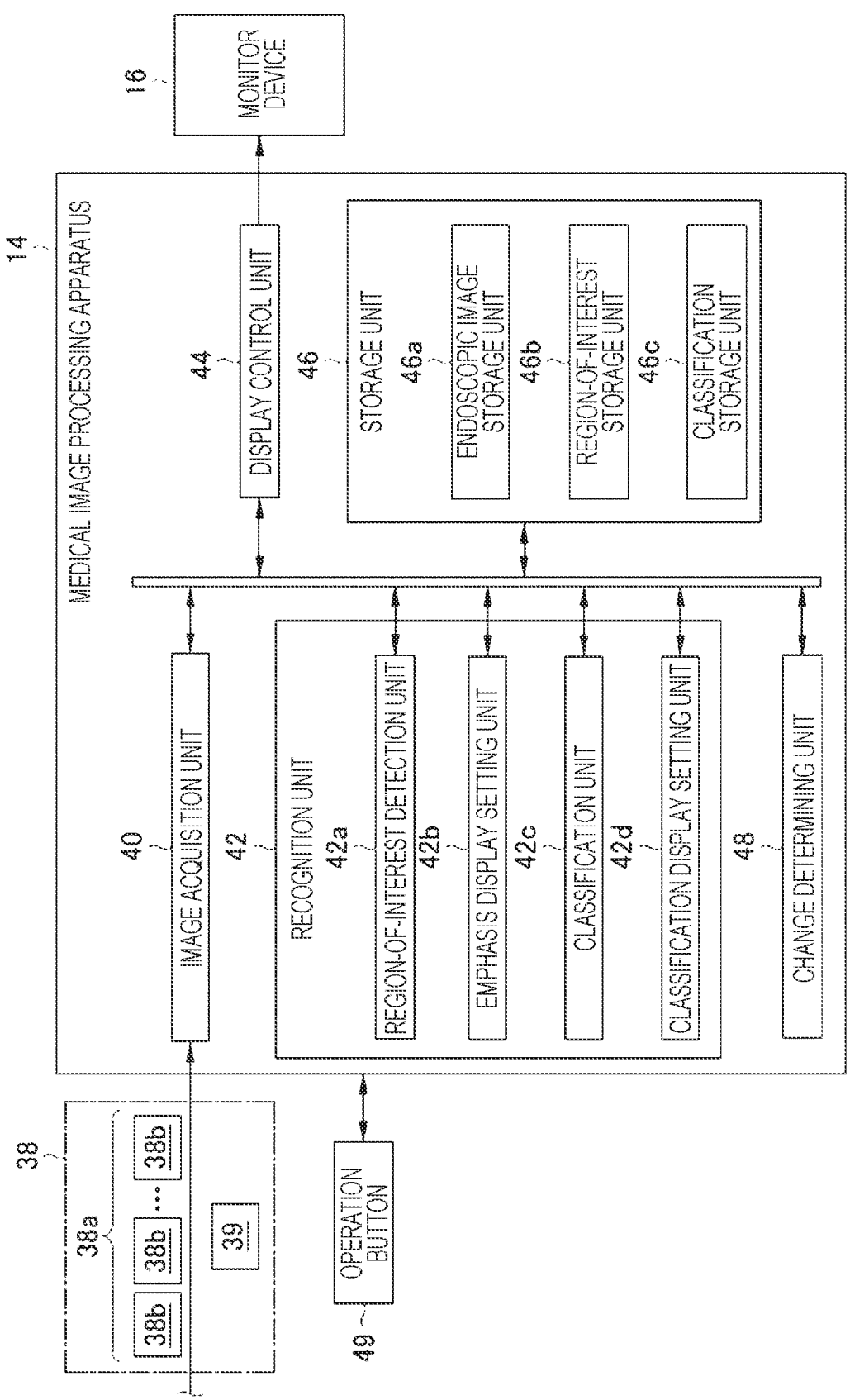
FIG. 3 is a functional block diagram of the medical image processing apparatus according to the embodiment.

The processor device 12 generates an endoscopic image 38, which is an observation image of the site to be observed, on the basis of the imaging signal acquired from the endoscope 10. Herein, the endoscopic image 38 includes a moving image. The endoscopic image 38 may include a still image 39. Note that a moving image, which is denoted by a reference sign 38a, is illustrated in FIG. 3. The endoscopic image 38 described in the embodiment is an example of a medical image.

When the still image capturing instruction part 32 of the operation section 21 is operated, the processor device 12 generates the still image 39 of the site to be observed on the basis of the imaging signal acquired from the imaging element 28 in parallel with generation of the moving image 38a. The still image 39 may be generated to have a resolution higher than the resolution of the moving image 38a.

When generating the endoscopic image 38, the processor device 12 performs image quality correction in which digital signal processing such as white balance adjustment and shading correction is used. The processor device 12 may add accessory information defined by the DICOM standard to the endoscopic image 38. Note that DICOM is an abbreviation for Digital Imaging and Communications in Medicine. The processor device 12 described in the embodiment is an example of a processor device including an endoscope control unit that controls an endoscope.

The processor device 12 outputs the endoscopic image 38 to each of the display device 13 and the medical image processing apparatus 14. The processor device 12 may output the endoscopic image 38 to a storage device (not illustrated) via a communication network (not illustrated) in accordance with a communication protocol compliant with the DICOM standard. Note that a communication network 140 illustrated in FIG. 2 may be used as the communication network.

The display device 13 is connected to the processor device 12. The display device 13 displays the endoscopic image 38 transmitted from the processor device 12. The technician may perform an operation of moving the insertion section 20 forward and backward while checking the endoscopic image 38 displayed on the display device 13. Upon detecting a lesion or the like at the site to be observed, the technician may operate the still image capturing instruction part 32 to capture a still image of the site to be observed.

A computer may be used as the medical image processing apparatus 14. A keyboard, a mouse, and the like connectable to the computer are used as the input device 15. The input device 15 and the computer may be connected to each other either with a cable or wirelessly. Various monitors connectable to the computer are used as the monitor device 16.

As the medical image processing apparatus 14, a diagnosis assisting apparatus such as a workstation or a server apparatus may be used. In this case, the input device 15 and the monitor device 16 are provided for each of a plurality of terminals connected to the workstation or the like. Further, as the medical image processing apparatus 14, a medical service assisting apparatus that assists creation of a medical report or the like may be used.

The medical image processing apparatus 14 acquires the endoscopic image 38 and stores the endoscopic image 38. The medical image processing apparatus 14 controls reproduction performed by the monitor device 16. Note that the term "image" used herein includes the meaning of an electric signal representing the image and the meaning of image data such as information representing the image. The term "image" used herein means at least any of an image itself or image data.

Further, the term "storing an image" can be read as "saving an image", "storage of an image", or the like. "Storing an image" used herein means "storing an image in a non-transitory manner". The medical image processing apparatus 14 may include a temporary storage memory that temporarily stores an image.

The input device 15 is used to input an operation instruction for the medical image processing apparatus 14. The monitor device 16 displays the endoscopic image 38 under the control of the medical image processing apparatus 14. The monitor device 16 may function as a display unit of various kinds of information in the medical image processing apparatus 14.

The medical image processing apparatus 14 may be connected to a storage device (not illustrated) via a communication network (not illustrated in FIG. 1). The DICOM standard, a protocol compliant with the DICOM standard, and the like may be used as the image storage format and for the communication between apparatuses via the communication network.

As the storage device (not illustrated), a storage or the like that stores data in a non-transitory manner may be used. The storage device may be managed by using a server apparatus (not illustrated). As the server apparatus, a computer that stores and manages various kinds of data may be used.

Hardware Configuration of Medical Image Processing Apparatus

Figure 2:
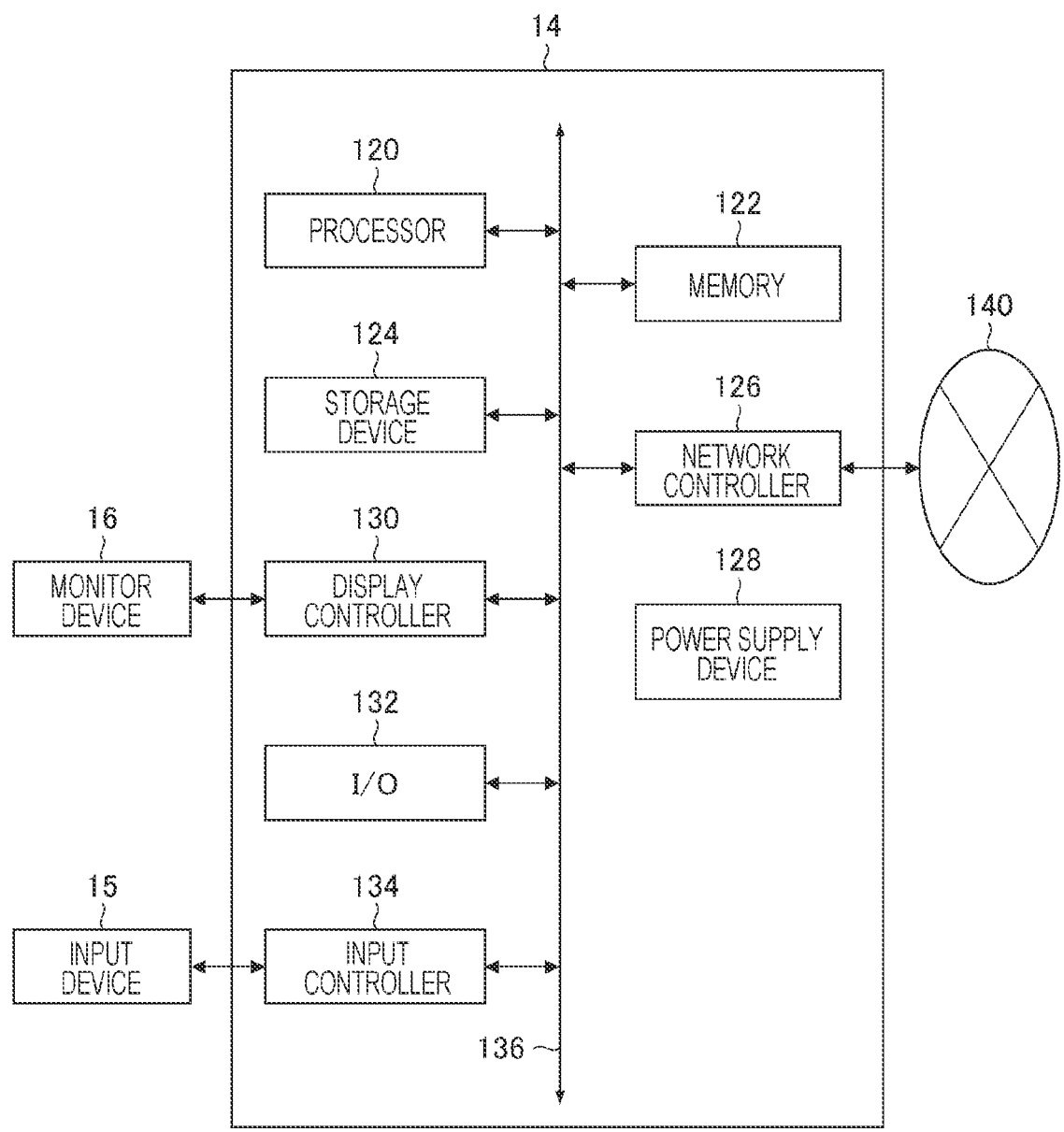
FIG. 2 is a block diagram illustrating a hardware configuration of the medical image processing apparatus.

FIG. 2 is a block diagram illustrating a hardware configuration of the medical image processing apparatus. The medical image processing apparatus 14 illustrated in FIG. 2 includes a processor 120, a memory 122, a storage device 124, a network controller 126, a power supply device 128, a display controller 130, an input/output interface 132, and an input controller 134. Note that I/O illustrated in FIG. 2 represents the input/output interface.

The processor 120, the memory 122, the storage device 124, the network controller 126, the display controller 130, and the input/output interface 132 are connected to each other via a bus 136 so that data communication can be performed therebetween.

Processor

The processor 120 functions as an overall control unit, various calculation units, and a storage control unit of the medical image processing apparatus 14. The processor 120 executes a program stored in a ROM (read only memory) included in the memory 122.

The processor 120 may download a program from an external storage device (not illustrated) via the network controller 126 and execute the downloaded program. The external storage device may be communicably connected to the medical image processing apparatus 14 via the communication network 140.

The processor 120 uses, as a calculation area, a RAM (random access memory) included in the memory 122 and executes various processes in cooperation with various programs. Consequently, various functions of the medical image processing apparatus 14 are implemented.

The processor 120 controls reading out of data from the storage device 124 and writing of data to the storage device 124. The processor 120 may acquire various kinds of data from an external storage device via the network controller 126. The processor 120 is capable of executing various processes such as calculations by using the acquired various kinds of data.

The processor 120 may include one or two or more devices. Examples of the devices include an FPGA (Field Programmable Gate Array), a PLD (Programmable Logic Device), and so on. An FPGA and a PLD are devices whose circuit configurations are changeable after being manufactured.

Other examples of the devices include an ASIC (Application Specific Integrated Circuit). An ASIC includes a circuit configuration dedicatedly designed to perform specific processing.

The processor 120 may use two or more devices of the same kind. For example, the processor 120 may use two or more FPGAs or two or more PLDs. The processor 120 may use two or more devices of different kinds. For example, the processor 120 may use one or more FPGAs and one or more ASICs.

When the medical image processing apparatus 14 includes the plurality of processors 120, the plurality of processors 120 may be configured by using a single device. As an example of configuring the plurality of processors 120 by using a single device, there is a form in which the single device is configured by using a combination of one or more CPUs (Central Processing Units) and software and this device functions as the plurality of processors 120. Note that software used herein is synonymous with a program.

Other examples of configuring the plurality of processors 120 by using a single device include a form in which a device that implements, with a single IC chip, the functions of the entire system including the plurality of processors 120. Representative examples of the device that implements, with a single IC chip, the functions of the entire system including the plurality of processors 120 include a SoC (System On Chip). Note that IC is an abbreviation for Integrated Circuit. As described above, the processor 120 is configured by using one or more of various devices as the hardware structure.

Memory

The memory 122 includes a ROM (not illustrated) and a RAM (not illustrated). The ROM stores various programs to be executed in the medical image processing apparatus 14. The ROM stores parameters, files, and the like used for executing various programs. The RAM functions as a temporary data storage area, a work area for the processor 120, and the like.

Storage Device

The storage device 124 stores various kinds of data in a non-transitory manner. The storage device 124 may be externally attached to the medical image processing apparatus 14. Instead of or along with the storage device 124, a large-capacity semiconductor memory device may be used.

Network Controller

The network controller 126 controls data communication between the medical image processing apparatus 14 and an external apparatus. The control of the data communication may include management of the traffic in the data communication. As the communication network 140 to which the medical image processing apparatus 14 is connected via the network controller 126, a known communication network such as a LAN (Local Area Network) may be used.

Power Supply Device

As the power supply device 128, a large-capacity power supply device such as a UPS (Uninterruptible Power Supply) is used. The power supply device 128 supplies power to each unit of the medical image processing apparatus 14 when the commercial power supply is cut off due to a power failure or the like.

Display Controller

The display controller 130 functions as a display driver that controls the monitor device 16 on the basis of a command signal transmitted from the processor 120.

Input/Output Interface

The input/output interface 132 communicably connects the medical image processing apparatus 14 and an external device to each other. A communication standard such as USB (Universal Serial Bus) may be used for the input/output interface 132.

Input Controller

The input controller 134 converts the format of a signal input by using the input device 15 into a format suitable for processing performed by the medical image processing apparatus 14. Information input from the input device 15 via the input controller 134 is transmitted to each unit via the processor 120.

Note that the hardware configuration of the medical image processing apparatus 14 illustrated in FIG. 2 is merely an example. Thus, addition, deletion, and modification may be appropriately made. In addition, the hardware configuration illustrated in FIG. 2 may also be used for the processor device 12 illustrated in FIG. 1.

Functional Blocks of Medical Image Processing Apparatus

FIG. 3 is a functional block diagram of the medical image processing apparatus according to the embodiment. The medical image processing apparatus 14 includes an image acquisition unit 40, a recognition unit 42, a display control unit 44, a storage unit 46, and a change determining unit 48. Note that in the present embodiment, the processor 120 of the medical image processing apparatus 14 illustrated in FIG. 2 functions as the image acquisition unit 40, the recognition unit 42, the display control unit 44, and the change determining unit 48. In addition, the storage device 124 illustrated in FIG. 2 functions as the storage unit 46. Note that the functions of the image acquisition unit 40, the recognition unit 42, the display control unit 44, and the change determining unit 48 may be implemented by a combination of one or a plurality of general-purpose processors (for example, microprocessors) and one or a plurality of special-purpose processors (for example, ASICs or FPGAs).

Image Acquisition Unit

The image acquisition unit 40 acquires, from the processor device 12, the endoscopic image 38 obtained by imaging using the endoscope 10. The image acquisition unit 40 stores the endoscopic image 38 in an endoscopic image storage unit 46a.

The image acquisition unit 40 may acquire the endoscopic image 38 from the processor device 12 via an information storage medium such as a memory card. The image acquisition unit 40 may acquire the endoscopic image 38 via the communication network 140 illustrated in FIG. 2.

The image acquisition unit 40 may acquire the moving image 38a constituted by time-series frame images 38b. The image acquisition unit 40 may acquire the still image 39 in the case where still image capturing is performed during capturing of the moving image 38a.

Recognition Unit

The recognition unit 42 includes a region-of-interest detection unit 42a, an emphasis display setting unit 42b, a classification unit 42c, and a classification display setting unit 42d. The recognition unit 42 uses a learning model of a CNN (Convolutional Neural Network) or the like to detect a region of interest from the endoscopic image 38. The recognition unit 42 sets emphasis display for emphasizing the region of interest. The recognition unit 42 uses learning model to classify the region of interest.

The region-of-interest detection unit 42a detects a region of interest from the endoscopic image 38 acquired by using the image acquisition unit 40. The region-of-interest detection unit 42a uses a trained learning model that has performed learning using a pair of the endoscopic image 38 and a region of interest in the endoscopic image 38 as correct answer data. The region-of-interest detection unit 42a stores the region of interest detected from the endoscopic image 38 in a region-of-interest storage unit 46b.

The emphasis display setting unit 42b sets emphasis display for emphasizing the region of interest detected from the endoscopic image 38. The emphasis display setting unit 42b identifies the position and size of the region of interest, and identifies the position and size of emphasis display in accordance with the position and size of the region of interest. The emphasis display setting unit 42b stores emphasis display information including the position and size of the emphasis display in association with the region of interest.

The emphasis display setting unit 42b may use a closed curve surrounding the region of interest as the emphasis display. As the closed curve surrounding the region of interest, a polygon such as a quadrangle surrounding the region of interest, a circle, and a closed curve of any shape may be used. As the closed curve surrounding the region of interest, a polygon or circle circumscribing the region of interest, a polygon or circle that coincides with the region of interest, and a polygon or circuit including the region of interest therein in noncontact manner may be used.

The classification unit 42c classifies the region of interest. For example, the classification unit 42c classifies whether the region of interest is a lesion or a non-lesion. The classification unit 42c may identify a disease name for the region of interest which is a lesion. The classification unit 42c may use standardized classification such as UICC (Union for International Cancer Control) and TNM classification. The classification unit 42c stores a classification for each region of interest in a classification storage unit 46c in association with information on the region of interest. The classification display setting unit 42d sets a display style of the region of interest classified by the classification unit 42c. For example, the classification display setting unit 42d sets whether the disease name identified for the region of interest by the classification unit 42c is displayed as a character string or a picture or icon. When displaying the disease name as a character string, the classification display setting unit 42d identifies the density, the color, and the size of the characters. The classification display setting unit 42d also identifies the display position of the classification for the region of interest.

Note that T of TNM is the initial for tumor. N of TNM is the initial for nodes. M of TNM is the initial for metastasis.

Display Control Unit

The display control unit 44 transmits, to the monitor device 16, a display signal representing an image or the like and causing the monitor device 16 to display the endoscopic image 38. The display control unit 44 transmits a display signal representing the region of interest and the classification for the region of interest to the monitor device 16. The display control unit 44 transmits a control signal for the monitor device 16, to the monitor device 16.

The monitor device 16 displays the endoscopic image 38, the region of interest, and the classification for the region of interest. The monitor device 16 may display the region of interest and the classification for the region of interest to be superimposed on the endoscopic image 38. The monitor device 16 may display the region of interest and the classification for the region of interest in a region defined as a region in which the endoscopic image 38 is displayed. The display control unit 44 updates display of the endoscopic image 38, display of the region of interest, and display of the classification for the region of interest by using predetermined update intervals.

Storage Unit

The storage unit 46 includes the endoscopic image storage unit 46a, the region-of-interest storage unit 46b, and the classification storage unit 46c. The endoscopic image storage unit 46a stores the endoscopic image 38 acquired by using the image acquisition unit 40.

The region-of-interest storage unit 46b stores information on the region of interest. The region-of-interest storage unit 46b may store information on the region of interest associated with the endoscopic image 38 from which the region of interest is detected. As the information on the region of interest, coordinate values of the region of interest in the endoscopic image 38 and the shape of the region of interest may be used.

As the coordinate values of the region of interest, the coordinate values of emphasis display used when the emphasis display is set may be used. The shape of the region of interest may include the style of the region of interest and the area of the region of interest.

The classification storage unit 46c stores a classification for each region of interest in association with information on the region of interest. As the information on the region of interest, a number, a symbol, or the like with which the region of interest can be identified may be used.

As the storage unit 46, one or more storage elements may be used. That is, the storage unit 46 may include three storage elements respectively corresponding to the endoscopic image storage unit 46a, the region-of-interest storage unit 46b, and the classification storage unit 46c. As each of the endoscopic image storage unit 46a, the region-of-interest storage unit 46b, and the classification storage unit 46c, a plurality of storage elements may be used. Further, two or all of the endoscopic image storage unit 46a, the region-of-interest storage unit 46b, and the classification storage unit 46c may be constituted by a single storage element.

Change Determining Unit

The change determining unit 48 determines whether to change at least any of the display style of the emphasis display or the display style of the classification for the region of interest. In response to acquisition of a command signal indicating that the display style of the emphasis display is to be changed, the change determining unit 48 may determine to change the display style of the emphasis display.

The change determining unit 48 transmits, to the display control unit 44, a command signal indicating that the display style of the emphasis display is to be changed. The display control unit 44 changes the display style of the emphasis display in accordance with the received command signal.

Note that the change determining unit 48 described in the embodiment may include, as a constituent element, a command signal acquisition unit that acquires a command signal transmitted when an operation section is operated.

For example, when a technician operates an operation button 49 of a holding portion held by the technician, a signal indicating that the display style of the emphasis display is to be changed is transmitted from the endoscope 10 to the medical image processing apparatus 14. When the medical image processing apparatus 14 receives the signal transmitted from the endoscope 10, the medical image processing apparatus 14 may change the display style of the emphasis display. Example of the holding portion held by the technician include the operation section 21 illustrated in FIG. 1.

Examples of changing the display style of the emphasis display include examples of reducing the intensity of emphasis display without setting the emphasis display in the off state, such as reducing the density of the emphasis display to make the emphasis display fainter, changing the color of the emphasis display to a lighter color, changing the solid line to a broken line or the like when the solid-line closed curve is used, and moving the emphasis display. When the intensity of the emphasis display is reduced without setting the emphasis display in the off state, the emphasis display is preferably weakened to be visually recognizable.

In addition, in the case where it is recognized that the region of interest is being classified by the technician, the medical image processing apparatus 14 may change the display style of the emphasis display. Examples of the case where the region of interest is being classified by the technician includes a case where normal light is changed to special light.

Note that the change determining unit 48 described in the embodiment may include, as a constituent element, a classification performing signal acquisition unit that acquires a classification performing signal indicating whether the region of interest is being classified.

In addition, in the case where it is recognized that a treatment operation is being performed, the medical image processing apparatus 14 may change the display style of the emphasis display. Examples of the case where it is recognized that a treatment operation is being performed include a case where a treatment tool is in the endoscopic image 38.

Note that the change determining unit 48 described in the embodiment may include, as a constituent element, a treatment tool operation determining unit that determines whether a treatment tool is being operated.

In response to acquisition of a command signal indicating that the display style of a classification for a region of interest is to be changed, the change determining unit 48 may determine to change the display style of the classification for the region of interest. The change determining unit 48 transmits, to the display control unit 44, a command signal indicating that the display style of the classification for the region of interest is to be changed. The display control unit 44 changes the display style of the classification for the region of interest in accordance with the received command signal.

For example, when a technician operates the operation button 49 of the holding portion held by the technician, a signal indicating that the display style of the classification for the region of interest is to be changed is transmitted from the endoscope 10 to the medical image processing apparatus 14. When the medical image processing apparatus 14 receives the signal transmitted from the endoscope 10, the medical image processing apparatus 14 may change the display style of the classification for the region of interest.

Examples of changing the display style of the classification for the region of interest include an example of reducing the density of characters representing the classification, an example of changing the color of characters representing the classification to a lighter color, an example of reducing the size of the characters representing the classification, and an example of moving characters representing the classification. Other examples of changing the display style of the classification for the region of interest include an example of omitting part of the character string representing the classification, an example of changing the character string to a picture or icon, or the like. Examples of omitting part of the character string include an example of using an abbreviation for the character string and an example of using the initial for the character string.

Procedure of Medical Image Processing Method

Figure 4:
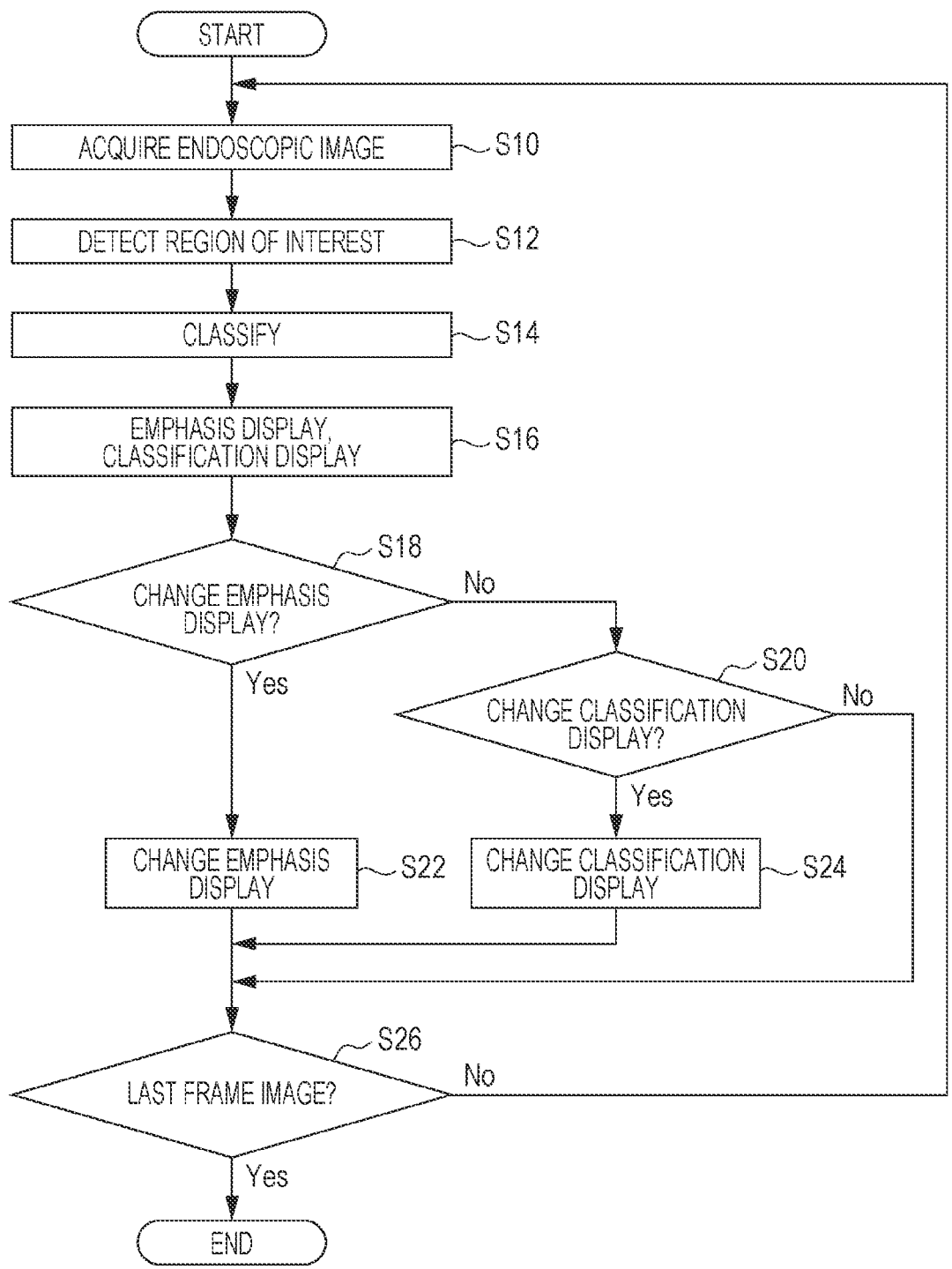
FIG. 4 is a flowchart illustrating a procedure of a medical image processing method according to the embodiment.

FIG. 4 is a flowchart of a procedure of a medical image processing method according to the embodiment. The medical image processing method described below may be used for the endoscopic image 38 acquired in an examination performed using the endoscope 10 or may be used for the endoscopic image 38 acquired from a medical image server or the like.

In an endoscopic image acquisition step S10, the image acquisition unit 40 illustrated in FIG. 3 acquires the endoscopic image 38 from the processor device 12 illustrated in FIG. 1. In the endoscopic image acquisition step S10, the image acquisition unit 40 stores the endoscopic image 38 in the endoscopic image storage unit 46*a*. After the endoscopic image acquisition step S10, the process proceeds to a region-of-interest detection step S12.

In the region-of-interest detection step S12, the region-of-interest detection unit 42*a* detects a region of interest from any of the frame images 38*b* of the moving image 38*a* that constitutes the endoscopic image 38. The region-of-interest detection unit 42*a* may detect a plurality of regions of interest from a single frame image 38*b*.

In the region-of-interest detection step S12, the region-of-interest detection unit 42*a* may detect a region of interest from all the frame images 38*b* of the moving image 38*a* or may detect a region of interest from the frame images 38*b* at predetermined intervals.

In the region-of-interest detection step S12, the region-of-interest detection unit 42*a* stores the region of interest in the region-of-interest storage unit 46*b* in association with information on the frame image 38*b*. After the region-of-interest detection step S12, the process proceeds to a classification step S14. Note that the region-of-interest detection step S12 corresponds to an example of a recognition step of detecting a region of interest.

In the classification step S14, the classification unit 42*c* classifies each region of interest. In the classification step S14, the classification unit 42*c* stores a classification for each region of interest in the classification storage unit 46*c* in association with the region of interest. After the classification step S14, the process proceeds to a display step S16. Note that the classification step S14 corresponds to an example of a recognition step of classifying a region of interest.

In the display step S16, the emphasis display setting unit 42*b* sets emphasis display for each region of interest and transmits information on the emphasis display to the display control unit 44. The display control unit 44 causes emphasis display to be displayed in the screen displaying the endoscopic image 38.

The classification unit 42*c* transmits information on the classification for each region of interest to the classification display setting unit 42*d*. In the display step S16, and the classification display setting unit 42*d* sets the display style of the classification for each region of interest and transmits information on the display style of the classification to the display control unit 44. The display control unit 44 causes the classification for each region of interest to be displayed in the screen displaying the endoscopic image 38. After the display step S16, the process proceeds to an emphasis display change determining step S18.

In the emphasis display change determining step S18, the change determining unit 48 determines whether to change the display style of the emphasis display. If the change determining unit 48 determines not to change the display style of the emphasis display in the emphasis display change determining step S18, No is determined and the process proceeds to a classification display change determining step S20. On the other hand, if the change determining unit 48 determines to change the display style of the emphasis display in the emphasis display change determining step S18, Yes is determined and the process proceeds to an emphasis display change step S22.

In the classification display change determining step S20, the change determining unit 48 determines whether to change the display style of the classification. If the change determining unit 48 determines not to change the display style of the classification in the classification display change determining step S20, No is determined and the process proceeds to a last frame image determining step S26.

On the other hand, if the change determining unit 48 determines to change the display style of the classification in the classification display change determining step S20, Yes is determined and the process proceeds to a classification display change step S24. Note that the order of the emphasis display change determining step S18 and the classification display change determining step S20 may be switched.

In the emphasis display change step S22, the emphasis display setting unit 42*b* transmits, to the display control unit 44, a command signal representing information on the emphasis display for which the display style is changed. The display control unit 44 changes the display style of the emphasis display in accordance with the received command signal. After the emphasis display change step S22, the process proceeds to the last frame image determining step S26.

In the classification display change step S24, the classification display setting unit 42d transmits, to the display control unit 44, a command signal representing information on the display style of the classification for the region of interest for which the display style is changed. The display control unit 44 changes the display style of the classification for the region of interest on the basis of the received command signal. After the classification display change step S24, the process proceeds to the last frame image determining step S26.

In the last frame image determining step S26, the medical image processing apparatus 14 determines whether the displayed endoscopic image 38 is the last frame image. If the medical image processing apparatus 14 determines that the displayed endoscopic image 38 is not the last frame image in the last frame image determining step S26, No is determined and the process returns to the endoscopic image acquisition step S10. Thereafter, the individual steps from the endoscopic image acquisition step S10 to the last frame image determining step S26 are repeatedly performed until Yes is determined in the last frame image determining step S26.

On the other hand, if the medical image processing apparatus 14 determines that the displayed endoscopic image 38 is the last frame image in the last frame image determining step S26, Yes is determined and the medical image processing apparatus 14 ends the medical image processing method.

Specific Examples of Changing Display Style of Emphasis Display and Changing Display Style of Classification Specific examples of changing the display style of the emphasis display and changing the display style of the classification will be described next. In the following description, any of the frame images 38b in the moving image 38a obtained by observing the large intestine by using the endoscope 10 illustrated in FIG. 1 is presented as an example. Note that the observation target is not limited to the large intestine, and the gullet, the stomach, the small intestine, and so on may be set as observation targets.

Figure 5:
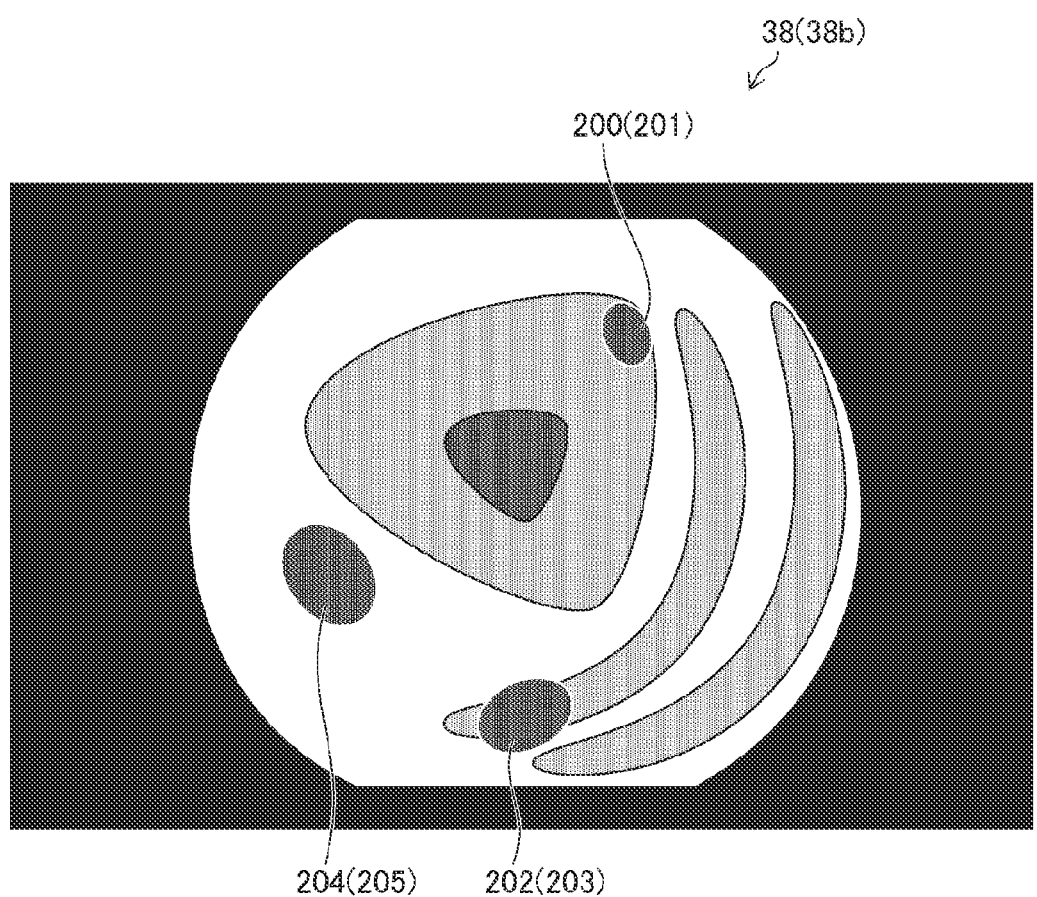
FIG. 5 is an explanatory diagram of an endoscopic image.

FIG. 5 is an explanatory diagram of an endoscopic image. In the endoscopic image 38 illustrated in FIG. 5, a first lesion 200, a second lesion 202, and a third lesion 204 are visually recognized. Although illustration is omitted in FIG. 5, the screen in which the endoscopic image 38 is displayed may include a region for displaying patient information, a region for displaying operation buttons, etc.

The region-of-interest detection unit 42a illustrated in FIG. 3 detects the first lesion 200 as a first region of interest 201. Likewise, the region-of-interest detection unit 42a detects the second lesion 202 as a second region of interest 203 and detects the third lesion 204 as a third region of interest 205.

Figure 6:
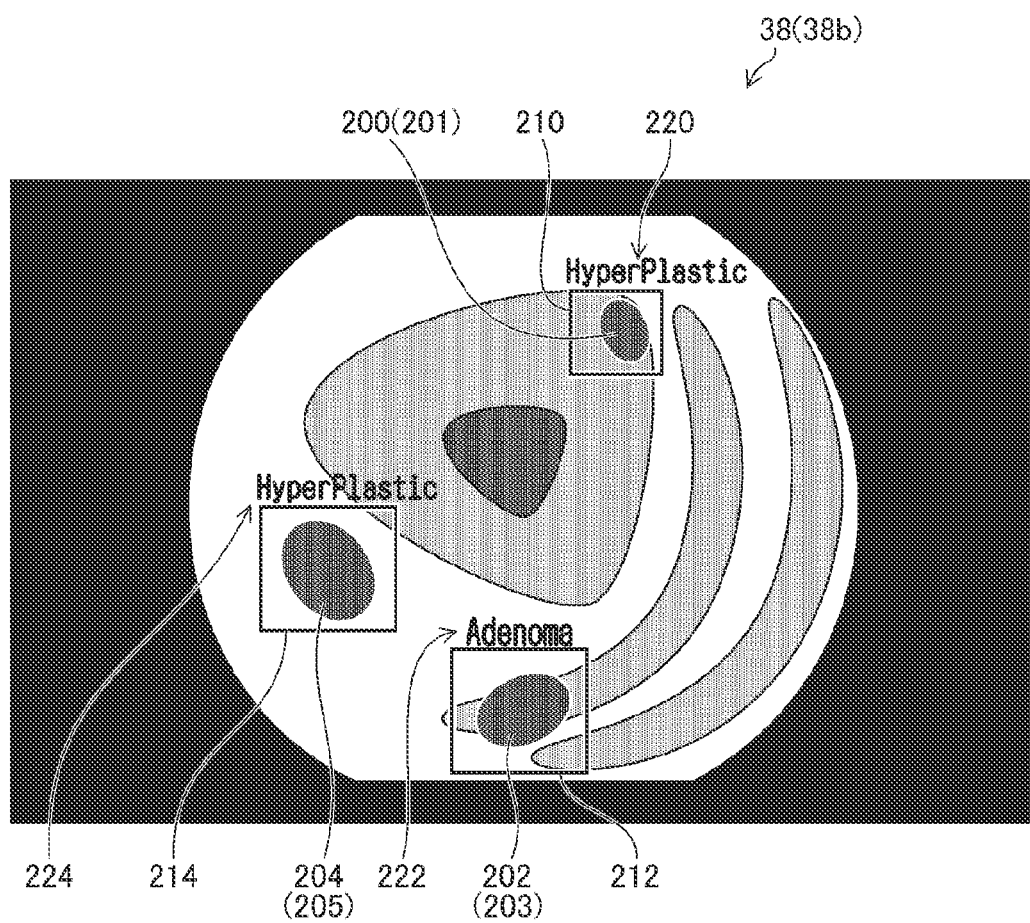
FIG. 6 is an explanatory diagram of emphasis display of regions of interest and classification display of the regions of interest.

FIG. 6 is an explanatory diagram of emphasis display of regions of interest and classification display of the regions of interest. In the endoscopic image 38 illustrated in FIG. 6, emphasis display of the regions of interest and classifications for the regions of interest are displayed in a screen identical to the screen displaying the endoscopic image 38. This allows a technician to visually recognize the endoscopic image 38, the emphasis display of the regions of interest, and the classifications for the regions of interest without moving their line of sight.

In the endoscopic image 38, a bounding box is used as the emphasis display of the region of interest. As the bounding box, a quadrangle surrounding the region of interest is used. That is, a first bounding box 210 is displayed to be superimposed on the first region of interest 201 corresponding to the first lesion 200.

Likewise, a second bounding box 212 is displayed to be superimposed on the second region of interest 203 corresponding to the second lesion 202. A third bounding box 214 is displayed to be superimposed on the third region of interest 205 corresponding to the third lesion 204.

In addition, in the endoscopic image 38, English text representing the kind of the lesion is displayed as the classification for the region of interest in a superimposed manner. That is, "Hyper Plastic" which is English text representing the hyperplastic polyp is displayed as a first classification 220 for the first region of interest 201 corresponding to the first lesion 200 at a position above the first bounding box 210.

Likewise, "Adenoma" which is English text representing the tumor is displayed as a second classification 222 for the second region of interest 203 corresponding to the second lesion 202 at a position above the second bounding box 212. In addition, "Hyper Plastic" which is English text representing the hyperplastic polyp is displayed as a third classification 224 for the third region of interest 205 corresponding to the third lesion 204 at a position above the third bounding box 214.

Specific Example of Changing Display Style of Emphasis Display

Figure 7:
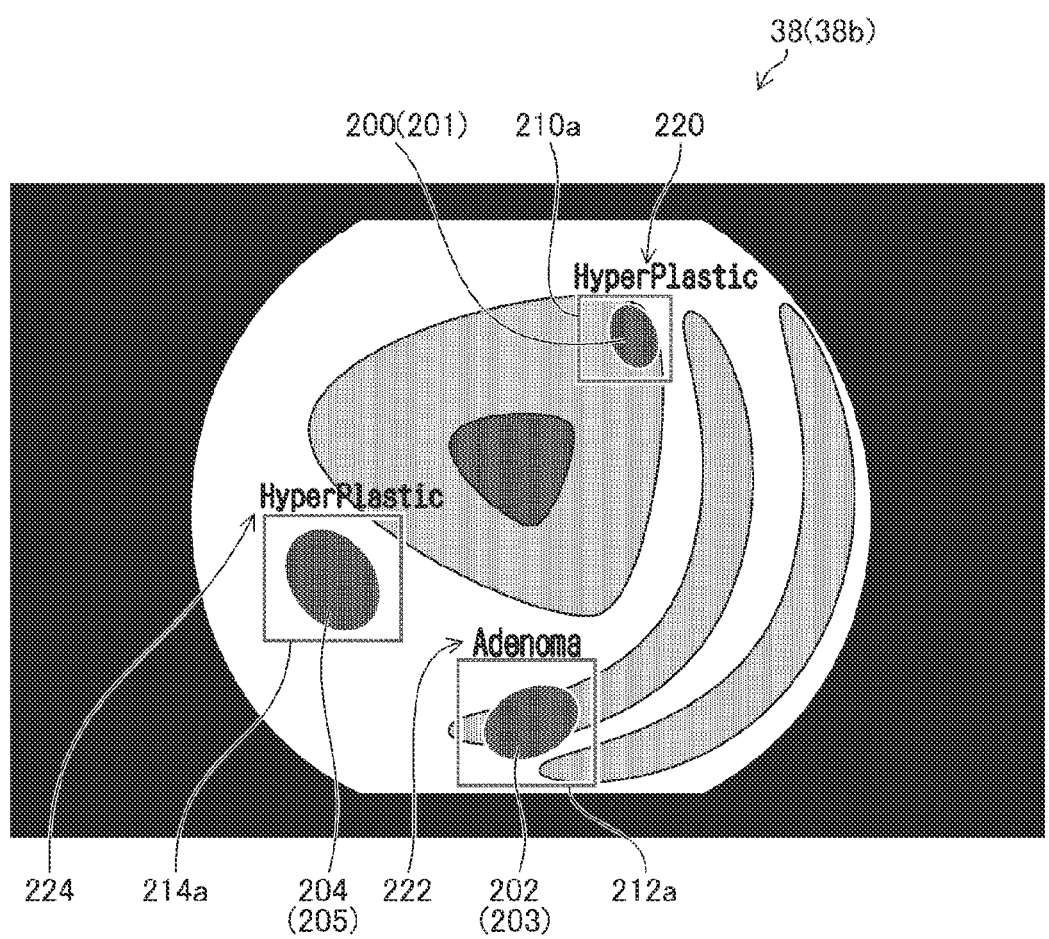
FIG. 7 is an explanatory diagram of a change in a display style of the emphasis display.

FIG. 7 is an explanatory diagram of a change in the display style of the emphasis display. In the endoscopic image 38 illustrated in FIG. 7, the degree of emphasis of emphasis display of the regions of interest is reduced. That is, a fourth bounding box 210a has a lower density and thus is fainter than the first bounding box 210 illustrated in FIG. 6.

Likewise, a fifth bounding box 212a has a lower density and thus is fainter than the second bounding box 212. A sixth bounding box 214a has a lower density and thus is fainter than the third bounding box 214.

The display style change for reducing the degree of emphasis of emphasis display may be implemented by changing color of the emphasis display. Examples of changing color of the emphasis display includes changing color from red to yellow, changing color from black to gray, etc.

Figure 8:
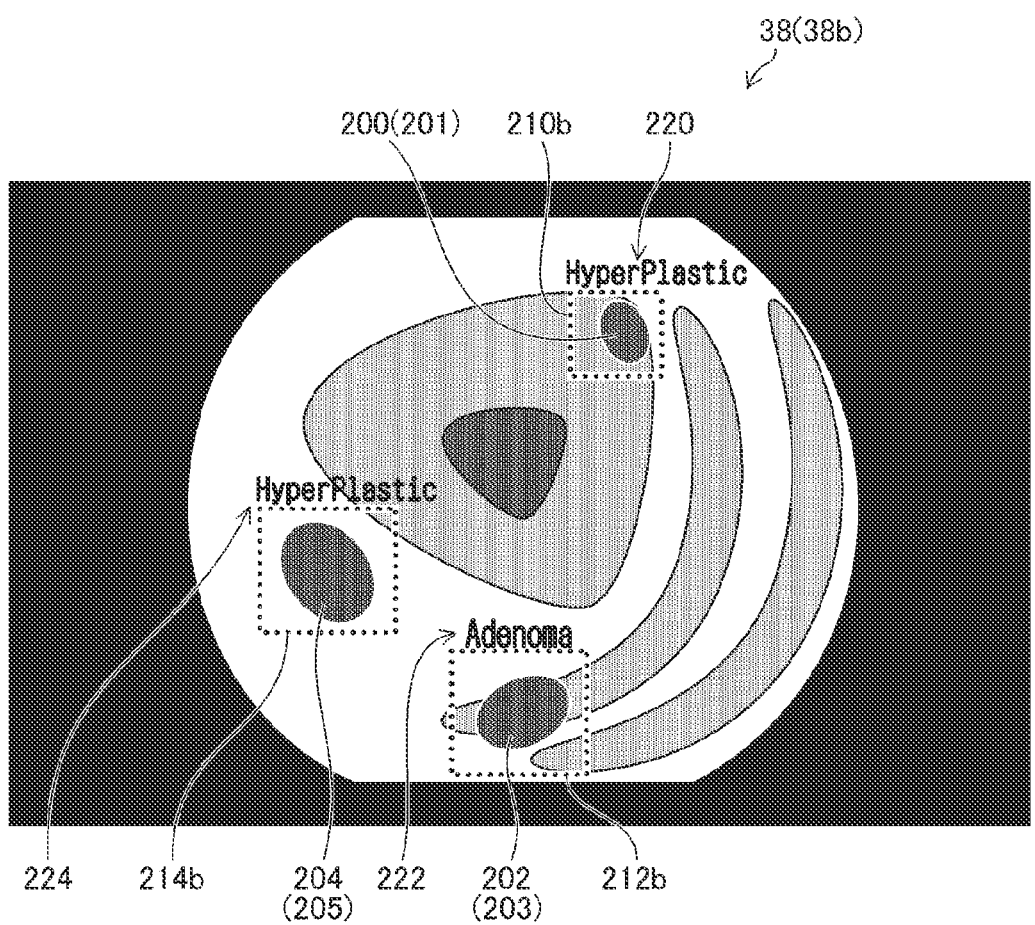
FIG. 8 is an explanatory diagram of another style change in the display style of the emphasis display.

FIG. 8 is an explanatory diagram of another style change in the display style of the emphasis display. In the endoscopic image 38 illustrated in FIG. 8, the type of the closed curve used for emphasis display is changed. That is, a broken line is used as the type of the line for a seventh bounding box 210b, an eighth bounding box 212b, and a ninth bounding box 214b.

Instead of or along with changing the type of the line, the thickness of the line may be changed. When the thickness of the line is reduced, the degree of emphasis is reduced.

Figure 9:
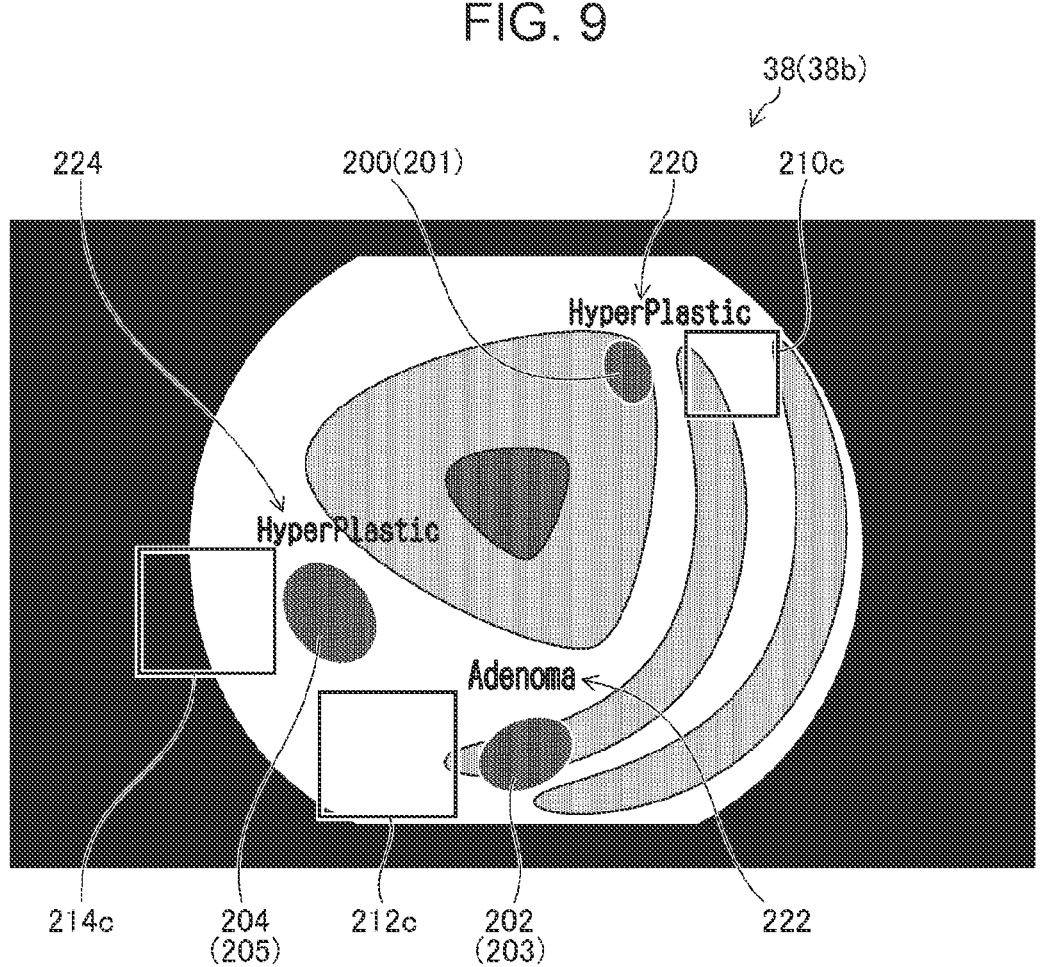
FIG. 9 is an explanatory diagram of a display style for moving a position of the emphasis display.

FIG. 9 is an explanatory diagram of a display style for moving a position of the emphasis display. In the endoscopic image 38 illustrated in FIG. 9, the positions of the bounding boxes are changed to positions at which the bounding boxes do not surround the respective regions of interest at all. That is, a tenth bounding box 210c is moved from a position where the bounding box surrounds the first region of interest 201 to a position where the bounding box does not surround the first region of interest 201.

Likewise, an eleventh bounding box 212c is moved from a position where the bounding box surrounds the second region of interest 203 to a position where the bounding box does not surround the second region of interest 203. A twelfth bounding box 214c is moved from a position where the bounding box surrounds the third region of interest 205 to a position where the bounding box does not surround the third region of interest 205.

Although illustration is omitted, the tenth bounding box 210c, the eleventh bounding box 212c, and the twelfth bounding box 214c may be moved to positions where the bounding boxes are not superimposed on the endoscopic image 38. The positions where the bounding boxes are not superimposed on the endoscopic image 38 described in the embodiment corresponds to an example of a position outside a display region of an image representing an observation target.

Specific Example of Changing Display Style of Classification

Figure 10:
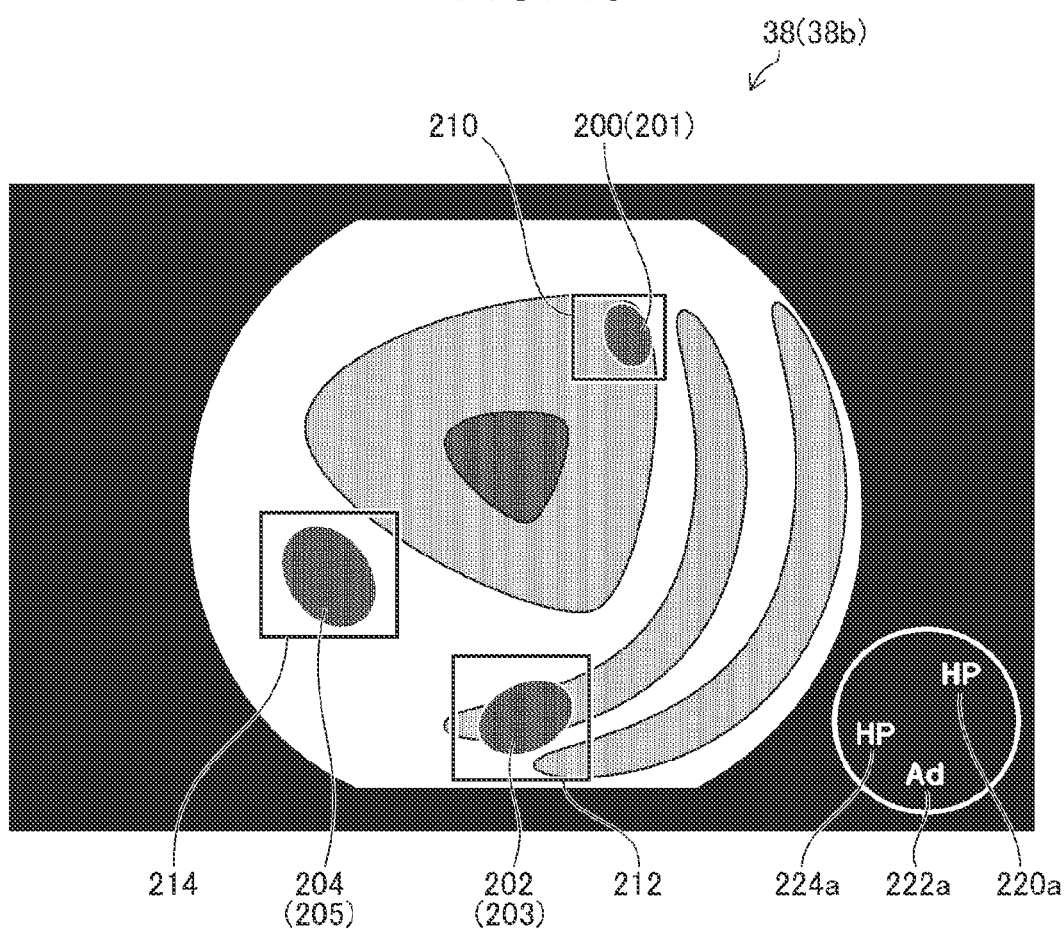
FIG. 10 is an explanatory diagram of a change in the display style of classifications.

FIG. 10 is an explanatory diagram of a change in the display style of classifications. A fourth classification 220a illustrated in FIG. 10 is moved from a position where the classification is superimposed on the endoscopic image 38 to a position where the classification is not superimposed on the endoscopic image 38. Likewise, a fifth classification 222a and a sixth classification 224a are moved from positions where the classifications are superimposed on the endoscopic image 38 to positions where the classifications are not superimposed on the endoscopic image 38.

In addition, a positional relationship among the first classification 220, the second classification 222, and the third classification 224 illustrated in FIG. 5 or the like is maintained as a positional relationship among the fourth classification 220a, the fifth classification 222a, and the sixth classification 224a.

Further, an abbreviation for omitting part of the character string used for the first classification 220 is used as the fourth classification 220a. Likewise, an abbreviation for omitting part of the character string used for the second classification 222 is used as the fifth classification 222a. An abbreviation for omitting part of the character string used for the third classification 224 is used as the sixth classification 224a.

Figure 11:
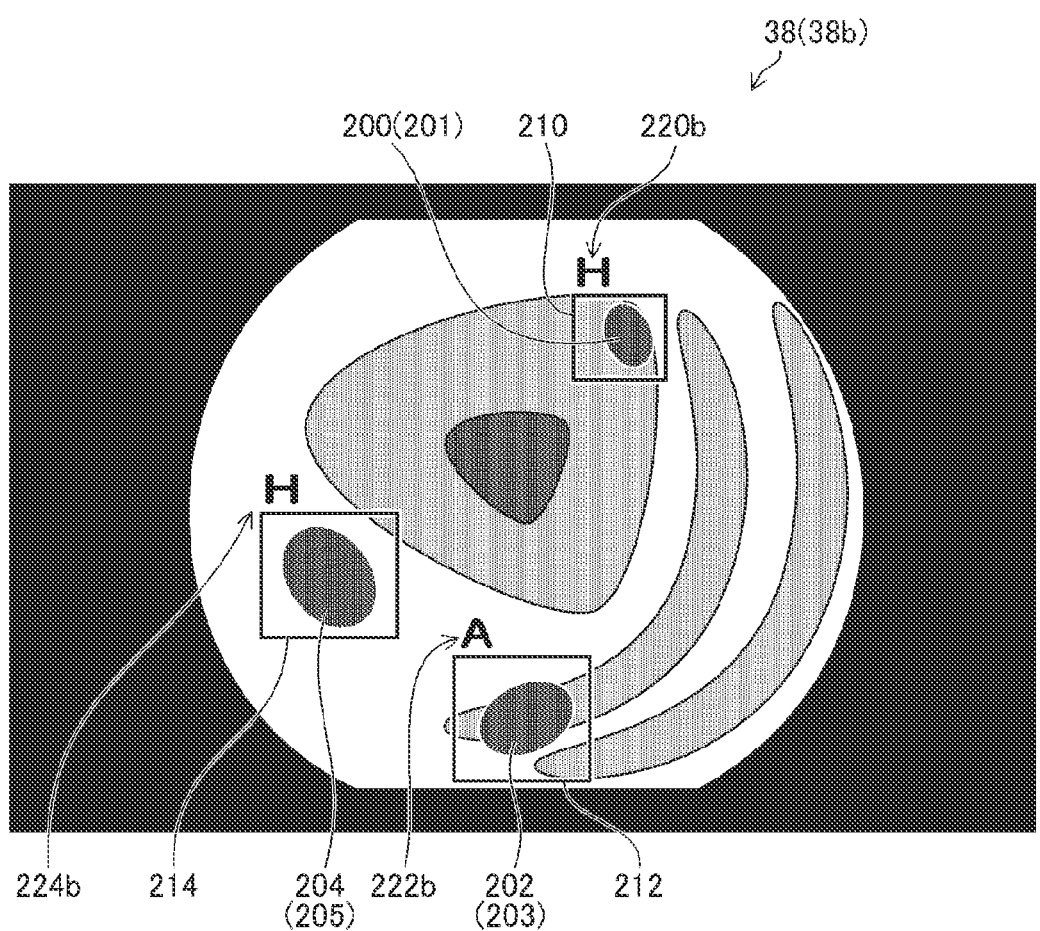
FIG. 11 is an explanatory diagram of another style change in the display style of the classifications.

FIG. 11 is an explanatory diagram of another style change in the display style of the classifications. The initial H of the character string "Hyper Plastic" used for the first classification 220 is used as a seventh classification 220b illustrated in FIG. 11. The initial A of the character string "Adenoma" used for the second classification 222 is used as an eighth classification 222b. The initial H of the character string "Hyper Plastic" used for the third classification 224 is used as a ninth classification 224b.

Specific Example of Convolutional Neural Network

Figure 12:
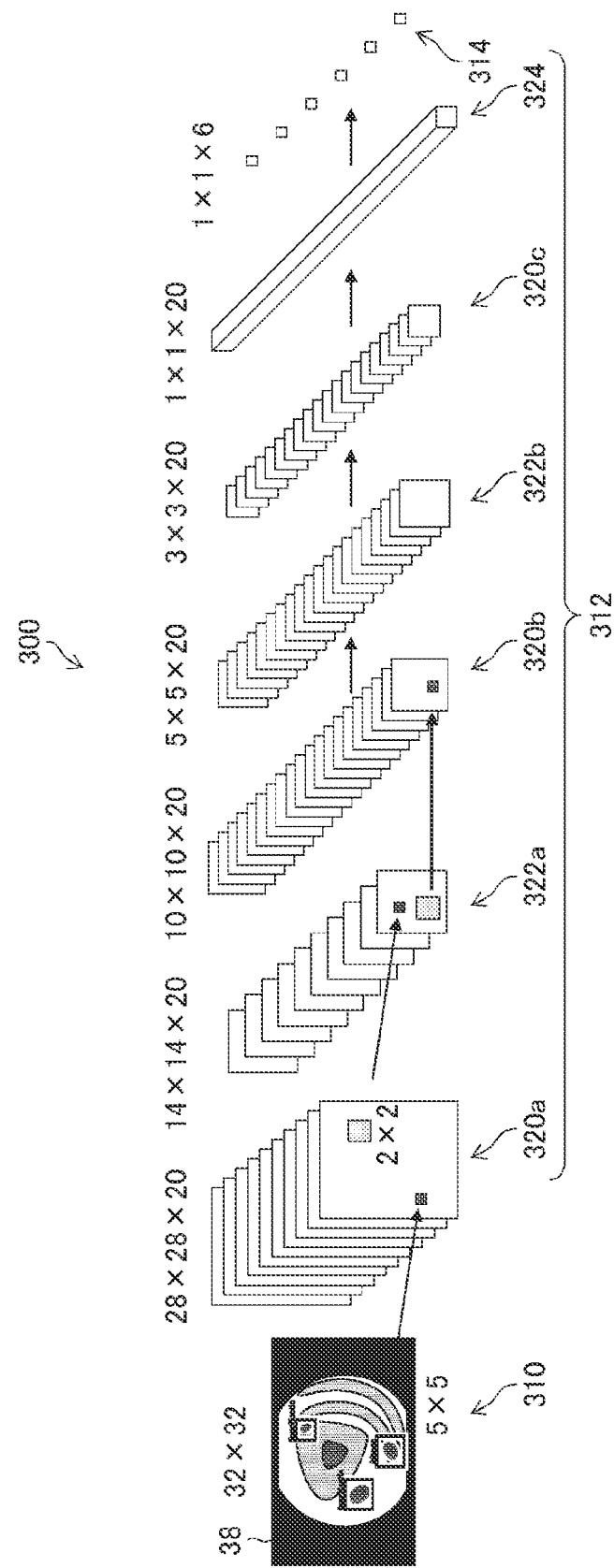
FIG. 12 is an explanatory diagram of a convolutional neural network.

FIG. 12 is an explanatory diagram of a convolutional neural network. A network 300 has a structure constituted by a plurality of layers and holds a plurality of weight parameters. The weight parameters are updated from initial values to optimum values, so that an untrained model becomes a trained model.

The network 300 includes an input layer 310, intermediate layers 312, and an output layer 314. The intermediate layers 312 include a first convolutional layer 320a, a first pooling layer 322a, a second convolutional layer 320b, a second pooling layer 322b, a third convolutional layer 320c, and a fully connected layer 324. Each layer has a structure in which a plurality of nodes are linked to each other by edges.

The endoscopic image 38 to be learned is input to the input layer 310. The intermediate layers 312 extract features from the endoscopic image 38. The first convolutional layer 320a, the second convolutional layer 320b, and the third convolutional layer 320c each perform filtering processing on the nodes in the previous layer to acquire a feature map. That is, the first convolutional layer 320a, the second convolutional layer 320b, and the third convolutional layer 320c each perform a convolutional operation using a filter on the nodes.

The first convolutional layer 320a generates, by using 20 filters, 20 feature maps having a 28×28 size from the endoscopic image 38 having a 32×32 size. The second convolutional layer 320b generates 20 feature maps having a 10×10 size from the 20 feature maps having a 14×14 size. The third convolutional layer 320c generates 20 feature maps having a 3×3 size from the 20 feature maps having a 5×5 size.

The first pooling layer 322a downsizes the feature maps output from the first convolutional layer 320a to generate new feature maps. The second pooling layer 322b downsizes the feature maps output from the second convolutional layer 320b to generate new feature maps.

The first pooling layer 322a generates the 20 feature maps having the 14×14 size from the 20 feature maps having the 28×28 size. The second pooling layer 322b generates the 20 feature maps having the 5×5 size from the 20 feature maps having the 10×10 size.

The first pooling layer 322a and the second pooling layer 322b play a role of providing the robustness so that the extracted features are not influenced by translation or the like. Note that the intermediate layers 312 are not limited to the case where a convolutional layer and a pooling layer constitute a single set. There may be a case where convolutional layers are consecutive and a configuration including a normalization layer (not illustrated).

The fully connected layer 324 connects all the outputs of the previous layer to all the nodes of the next layer. That is, the fully connected layer 324 connects outputs of the third convolutional layer 320c to all the nodes of the output layer 314.

The output layer 314 outputs features extracted using the intermediate layers 312 from the endoscopic image 38. The recognition unit 42 illustrated in FIG. 3 includes a network that extracts a region of interest from the endoscopic image 38 and a network that classifies the region of interest.

Any initial values are set as filter coefficients and offset values used in the first convolutional layer 320a or the like and as weights of connections in the fully connected layer 324 to the next layer in the network 300 before training.

The network 300 acquires an output result output from the output layer 314 and correct answer data for the output result and calculates an error between the output result and the correct answer data. Examples of the error calculation method include softmax entropy and sigmoid.

The network 300 adjusts the parameters of the network 300 by using error backpropagation on the basis of the calculated error. The network 300 repeatedly adjusts the parameters and performs learning until an error between the output result and the correct answer data becomes small.

The trained network 300 outputs at least any of a region of interest in an input image or a classification for the region of interest. The output result may be used as correct answer data, and the network 300 may be re-trained by using pairs of the input image and the output result.

The network that detects a region of interest from the endoscopic image 38 and the network that classifies the region of interest perform common processing in some of the intermediate layers 312. Accordingly, the network that detects a region of interest from the endoscopic image 38 and the network that classifies the region of interest may use some of the parameters of the intermediate layers 312 in common.

Although illustration is omitted, the recognition unit 42 includes a parameter storage unit that stores parameters used in the network that detects a region of interest from the endoscopic image 38 and parameters used in the network that classifies the region of interest.

The network that detects a region of interest from the endoscopic image 38 and the network that classifies the region of interest may identify the position of the region of interest and classify the region of interest on the basis of an overlapping degree of the feature maps.

The network that detects a region of interest from the endoscopic image 38 and the network that classifies the region of interest may collectively learn detection of a region of interest and classification of the region of interest for a single endoscopic image 38.

The plurality of convolutional layers described in the embodiment correspond to an example of a plurality of downsizing processing units that perform processing for reducing a size of an input image in stages. A combination of the plurality of convolutional layers and the plurality of pooling layers described in the embodiment corresponds to an example of a plurality of downsizing processing units that perform processing for reducing a size of an input image in stages.

The convolutional layer described in the embodiment corresponds to an example of a feature map generation unit that generates a feature map from an output image of each of the plurality of downsizing processing units.

The network 300 described in the embodiment corresponds to an example of a region-of-interest recognition unit that performs at least any of identification of a region of interest or classification of the region of interest from the feature maps.

The pooling layer described in the embodiment corresponds to a pooling processing unit that performs pooling processing on the input image. The convolutional layer described in the embodiment corresponds to an example of a convolutional processing unit.

Advantages

According to the medical image processing apparatus and the medical image processing method presented in the embodiment, the following advantages may be obtained.

[1]

A region of interest is detected from the endoscopic image 38, and emphasis display for emphasizing the region of interest is set. The region of interest is classified. The emphasis display and a classification are displayed to be superimposed on the endoscopic image 38. Whether to change a display style of the emphasis display is determined. If it is determined to change the display style of the emphasis display, the display style is changed to weaken the emphasis display. Whether to change a display style of the classification is determined. If it is determined to change the display style of the classification, the display style is changed to reduce visual recognizability of the classification. Consequently, when a technician observes an observation target, a situation may be suppressed in which the emphasis display and the classification hinder observation performed by the technician.

The display style is changed to reduce emphasis to a degree at which the emphasis display is visually recognizable without setting displaying of the emphasis display into an off state. Consequently, diagnosis assist that uses emphasis display can be utilized. The display style is changed to reduce the visual recognizability of the classification to a degree at which the classification is visual recognizable without setting displaying of the classification into an off state. Consequently, diagnosis assist that uses a classification can be utilized.

[2]

In the case where a technician operates an operation section, the display style of at least any of the emphasis display or the classification is changed. Consequently, the display style of at least any of the emphasis display or the classification can be changed on the basis of an operation by a technician.

[3]

In the case where the region of interest is being classified, the display style of at least any of the emphasis display or the classification is changed. Consequently, the display style of at least any of the emphasis display or the classification can be changed in the case where the region of interest is being classified.

[4]

In the case where a treatment tool is being operated, the display style of at least any of the emphasis display or the classification is changed. Consequently, the display style of at least any of the emphasis display or the classification can be changed in the case where the treatment tool is being operated.

[5]

A recognition unit uses a deep learning model such as a CNN. Consequently, the region-of-interest detection accuracy and the region-of-interest classification accuracy may improve. Re-training is performed by using region-of-interest detection results and region-of-interest classification results. Consequently, the region-of-interest detection accuracy and the region-of-interest classification accuracy may further improve.

[6]

The display style of the emphasis display is changed to weaken the emphasis display. Consequently, the visual recognizability of the emphasis display may be reduced.

[7]

A closed curve surrounding the region of interest is used as the emphasis display. At least any of changing a density of a line, changing a color, or changing a type of a line is used for changing the display style of the emphasis display. Consequently, the visual recognizability of the emphasis display may be reduced without greatly changing the emphasis display.

[8]

Moving the emphasis display to a position where the emphasis display is not superimposed on the endoscopic image 38 is used for changing the display style of the emphasis display. Consequently, the visual recognizability of the emphasis display may be reduced in a state in which the emphasis display is displayed.

[9]

Text information is used as classification information representing the content of the classification. Moving the text information to a position where the text information is not superimposed on the endoscopic image 38 is used for changing the display style of the classification. Consequently, the visual recognizability of the text information representing the content of the classification may be reduced in a state in which the text information representing the content of the classification is displayed.

[10]

In the case where a plurality of regions of interest are detected, a plurality of classifications for the plurality of regions of interest are moved while a positional relationship among the plurality of regions of interest is maintained. Consequently, the positional relationship among the plurality of regions of interest may be grasped by using the positional relationship among the plurality of classifications.

[11]

Text information is used as classification information representing the content of the classification. Part of the text information is omitted to change the display style of the classification. Consequently, the visual recognizability of the text information representing the content of the classification may be reduced in a state in which the text information representing the content of the classification is displayed.

[12]

Text information is used as classification information representing the content of the classification. Only the initial of the text information is displayed to change the display style of the classification. Consequently, the visual recognizability of the text information representing the content of the classification may be reduced in a state in which the text information representing the content of the classification is displayed.

MODIFICATIONS OF MEDICAL IMAGE PROCESSING APPARATUS

First Modification

The display style of the emphasis display of the region of interest and the display style of the classification may be selectively changed. For example, the operation section 21 may include a switch for switching between changing the display style of the region of interest and changing the display style of the classification, and changing the display style of the region of interest and changing the display style of the classification are switched between in accordance with an operation on the switch.

Second Modification

Displaying of the region of interest may be set in an off state when the display style of the region of interest is changed. Displaying of the classification may be set in an off state when the display style of the classification is changed. By using a switch cyclically operated, a standard display style, a display style for continuing the display but reducing the emphasis, and a display style for setting the display into the off state can be switched.

Third Modification

The display style of the region of interest may be returned to the standard display style after a predetermined period passes since the display style of the region of interest is changed. The display style of the classification may be returned to the standard display style after a predetermined period passes since the display style of the classification is changed. Any period may be set as the predetermined period.

Fourth Modification

An observation state with the endoscope 10 may be detected, and at least any of the display style of the region of interest and the display style of the classification may be automatically changed. For example, in the case of observation under normal light, emphasis display of the region of interest and the classification for the region of interest are displayed. In the case of observation under special light, emphasis display of the region of interest is unnecessary, and thus a change may be made to weaken the emphasis display of the region of interest.

Fifth Modification

When the endoscopic image 38 is enlarged for observation, the display style of the emphasis display of the region of interest is changed.

In processing for enlarging the emphasis display of the region of interest in accordance with enlargement of the endoscopic image 38, the emphasis display of the region of interest may become unnatural. Accordingly, when the endoscopic image 38 is enlarged for observation, the display style of the emphasis display of the region of interest is changed to reduce the visual recognizability of the emphasis display of the region of interest and thus reduce the load on the technician.

Modifications of Endoscope System

Modification of Processor Device

The processor device 12 may have the functions of the medical image processing apparatus 14. That is, the processor device 12 and the medical image processing apparatus 14 may be integrated together. In such an embodiment, the display device 13 may also serve as the monitor device 16. The processor device 12 may include a connection terminal to which the input device 15 is connected.

Modifications of Illumination Light

One example of the medical image acquirable by using the endoscope system 9 according to the present embodiment is a normal-light image acquired by radiating light in a white range or light in a plurality of wavelength ranges as the light in the white range.

Another example of the medical image acquirable by using the endoscope system 9 according to the present embodiment is an image acquired by radiating light in a specific wavelength range. A range narrower than the white range may be used as the specific wavelength range. The following modifications may be employed.

First Modification

A first example of the specific wavelength range is a blue range or a green range in a visible range. The wavelength range of the first example includes a wavelength range of 390 nm or more and 450 nm or less or a wavelength range of 530 nm or more and 550 nm or less, and the light of the first example has a peak wavelength in the wavelength range of 390 nm or more and 450 nm or less or the wavelength range of 530 nm or more and 550 nm or less.

Second Modification

A second example of the specific wavelength range is a red range in the visible range. The wavelength range of the second example includes a wavelength range of 585 nm or more and 615 nm or less or a wavelength range of 610 nm or more and 730 nm or less, and the light of the second example has a peak wavelength in the wavelength range of 585 nm or more and 615 nm or less or the wavelength range of 610 nm or more and 730 nm or less.

Third Modification

A third example of the specific wavelength range includes a wavelength range in which an absorption coefficient is different between oxyhemoglobin and deoxyhemoglobin, and the light of the third example has a peak wavelength in the wavelength range in which the absorption coefficient is different between oxyhemoglobin and deoxyhemoglobin. The wavelength range of this third example includes a wavelength range of 400±10 nm, a wavelength range of 440±10 nm, a wavelength range of 470±10 nm, or a wavelength range of 600 nm or more and 750 nm or less, and the light of the third example has a peak wavelength in the wavelength range of 400±10 nm, the wavelength range of 440±10 nm, the wavelength range of 470±10 nm, or the wavelength range of 600 nm or more and 750 nm or less.

Fourth Modification

A fourth example of the specific wavelength range is a wavelength range of excitation light that is used to observe fluorescence emitted by a fluorescent substance in a living body and excites this fluorescent substance. For example, the specific wavelength range of the fourth example is a wavelength range of 390 nm or more and 470 nm or less. Note that observation of fluorescence may be referred to as fluorescence observation.

Fifth Modification

A fifth example of the specific wavelength range is a wavelength range of infrared light. The wavelength range of this fifth example includes a wavelength range of 790 nm or more and 820 nm or less or a wavelength range of 905 nm or more and 970 nm or less, and the light of the fifth example has a peak wavelength in the wavelength range of 790 nm or more and 820 nm or less or the wavelength range of 905 nm or more and 970 nm or less.

Generation Example of Special-Light Image

The processor device 12 may generate a special-light image having information in the specific wavelength range on the basis of a normal-light image obtained through imaging using white light. Note that the term "generation" used herein includes "acquisition". In this case, the processor device 12 functions as a special-light image acquisition unit. The processor device 12 obtains a signal of the specific wavelength range by performing calculation based on color information of red, green, and blue or color information of cyan, magenta, and yellow included in the normal-light image.

Note that red, green, and blue are sometimes referred to as RGB. In addition, cyan, magenta, and yellow are sometimes referred to as CMY.

Generation Example of Feature-Quantity Image

As the medical image, a feature-quantity image may be generated by using calculation based on at least any of a normal-light image obtained by radiating light in the white range or light in a plurality of wavelength ranges as the light in the white range or a special-light image obtained by radiating light in the specific wavelength range.

In the embodiment and modifications described above, an endoscopic image is presented as an example of a medical image. However, a CT image or the like may be used as the medical image.

Application Example to Program for Causing Computer to Function as Image Processing Apparatus The above-described medical image processing method can be configured as a program that implements functions corresponding to respective steps of the medical image processing method by using a computer. For example, a program may be configured to cause a computer to implement a recognition function that detects a region of interest from the acquired endoscopic image 38 and classifies the region of interest, a display function that causes emphasis display for emphasizing the region of interest and a classification for the region of interest to be displayed in a screen identical to a screen displaying the endoscopic image 38, a change determining function that determines whether to change a display style of the emphasis display and whether to change a display style of the classification for the region of interest, in which the display function makes a change to reduce a degree of emphasis in a case where it is determined that the display style of the emphasis display is to be changed and makes a change to reduce visual recognizability of the classification in a case where it is determined that the display style of the classification is to be changed.

A program that causes a computer to implement the above-described image processing functions may be stored on a computer-readable information storage medium which is a non-transitory tangible information storage medium, and the program may be provided using the information storage medium.

In addition, instead of the configuration in which the program is stored on a non-transitory information storage medium and is provided, a configuration in which a program signal is provided via a communication network may be employed.

Combination of Embodiment, Modifications, Etc.

The constituent elements described in the embodiment above and the constituent elements described in the modifications can be appropriately used in combination, and some of the constituent elements can be replaced.

In the embodiment of the present invention described above, the constituent elements can be appropriately changed, added, or deleted within a scope not departing from the gist of the present invention. The present invention is not limited to the embodiment described above, and various modifications can be made by a person having the ordinary skill in the art within the technical sprit of the present invention.

REFERENCE SIGNS LIST 9 endoscope system
10 endoscope
11 light source device
12 processor device
13 display device
14 medical image processing apparatus
15 input device
16 monitor device
20 insertion section
21 operation section
22 universal cord
25 soft part
26 bending part
27 tip part
27a tip surface
28 imaging element
29 bending operation knob
30 air/water supply button
31 suction button
32 still image capturing instruction part
33 treatment tool introduction port
35 light guide
36 signal cable
37a connector
37b connector
38 endoscopic image
38a moving image
38b frame image
39 still image
40 image acquisition unit
42 recognition unit
42a region-of-interest detection unit
42b emphasis display setting unit
42c classification unit
42d classification display setting unit
44 display control unit
46 storage unit
46a endoscopic image storage unit
46b region-of-interest storage unit
46c classification storage unit
48 change determining unit
49 operation button
120 processor
122 memory
124 storage device
126 network controller
128 power supply device
130 display controller
132 input/output interface
134 input controller
136 bus
140 communication network
200 first lesion
201 first region of interest
202 second lesion
203 second region of interest
204 third lesion
205 third region of interest
210 first bounding box
210a fourth bounding box
210b seventh bounding box
210c tenth bounding box
212 second bounding box
212a fifth bounding box
212b eighth bounding box
212c eleventh bounding box
214 third bounding box
214a sixth bounding box
214b ninth bounding box
214c twelfth bounding box
220 first classification
220a fourth classification
220b seventh classification
222 second classification
222a fifth classification
222b eighth classification
224 third classification
224a sixth classification
224b ninth classification
300 network
310 input layer
312 intermediate layer
314 output layer
320a first convolutional layer
320b second convolutional layer
320c third convolutional layer
322a first pooling layer
322b second pooling layer
324 fully connected layer
S10 to S26 steps of medical image processing method

What is claimed is:

1. A medical image processing apparatus comprising:
a processor configured to
detect a region of interest from an acquired medical image and classify the detected region of interest;
display an emphasis display for emphasizing the region of interest and a classification for the region of interest on a screen identical to a screen for displaying an observation target included in the medical image;
determine at least any of whether to change a display style of the emphasis display or whether to change a display style of the classification; and
reduce a degree of emphasis of the emphasis display in a case where the display style of the emphasis display is determined to change and reduce visual recognizability of the classification in a case where the display style of the classification is determined to change.

2. The medical image processing apparatus according to claim 1,
wherein the processor is further configured to
acquire a command signal transmitted in a case where an operation section is operated, and
change the display style of the emphasis display in accordance with the command signal indicating that the display style of the emphasis display is to be changed and change the display style of the classification in accordance with the command signal indicating that the display style of the classification is to be changed.

3. The medical image processing apparatus according to claim 1,
wherein the processor is further configured to
acquire a classification performing signal indicating whether the region of interest is being classified, and
change the display style of the emphasis display in accordance with the classification performing signal indicating that the region of interest is being classified.

4. The medical image processing apparatus according to claim 1,
wherein the processor is further configured to
determine whether a treatment tool is being operated, and
change at least one of the display style of the emphasis display or the display style of the classification in a case where the treatment tool is being operated.

5. The medical image processing apparatus according to claim 1,
wherein the processor is further configured to
perform processing for reducing a size of an input image in stages; and
generate a feature map from an output image.

6. The medical image processing apparatus according to claim 5,
wherein the processor is further configured to perform pooling processing on the input image or convolutional processing on the input image.

7. The medical image processing apparatus according to claim 5,
wherein the processor is further configured to
perform at least any of detection of the region of interest or classification of the region of interest from a plurality of the generated feature maps.

8. The medical image processing apparatus according to claim 7,
wherein the processor is further configured to perform detection of the region of interest and classification of the region of interest on the basis of an overlapping degree of the plurality of feature maps.

9. The medical image processing apparatus according to claim 1,
wherein the processor is further configured to store parameters obtained by collectively learning detection of a region of interest and classification of the region of interest for at least one image in a storage.

10. The medical image processing apparatus according to claim 1,
wherein the processor is further configured to
use a closed curve surrounding the region of interest as the emphasis display, and
change at least any of a color, a density, or a type of a line of the closed curve when changing the display style of the emphasis display.

11. The medical image processing apparatus according to claim 1,
wherein the processor is further configured to move the emphasis display to a position where visual recognizability of the emphasis display is reduced when changing the display style of the emphasis display.

12. The medical image processing apparatus according to claim 1,
wherein the processor is further configured to
use text information representing content of the classification as classification information representing the classification for the region of interest, and
move the text information to a position where visual recognizability of the text information is reduced when changing the display style of the classification for the region of interest.

13. The medical image processing apparatus according to claim 12,
wherein the processor is further configured to move the text information to a position outside a display region of an image representing the observation target when changing the display style of the classification for the region of interest.

14. The medical image processing apparatus according to claim 13,
wherein in a case where a plurality of the regions of interest are detected, the processor is further configured to move a plurality of pieces of the text information representing classifications for the plurality of regions of interest to positions outside the display region of the image representing the observation target while maintaining a positional relationship among the plurality of regions of interest.

15. The medical image processing apparatus according to claim 12,
wherein when changing the display style of the classification for the region of interest, the processor is further configured to cause only an initial of a character string representing a meaning of the classification to be displayed as the text information.

16. An endoscope system comprising:
an endoscope;
a processor device that controls the endoscope; and
a medical image processing apparatus that performs processing on an endoscopic image acquired by using the endoscope,
wherein the medical image processing apparatus is configured to
detect a region of interest from an acquired medical image and classifies the detected region of interest;
display an emphasis display for emphasizing the region of interest and a classification for the region of interest on a screen identical to a screen for displaying an observation target included in the medical image;
determine at least any of whether to change a display style of the emphasis display or whether to change a display style of the classification, and
reduce a degree of emphasis of the emphasis display in a case where the the display style of the emphasis display is determined to change and reduce visual recognizability of the classification in a case where the display style of the classification is determined to change.

17. A medical image processing method comprising:
detecting a region of interest from an acquired medical image and classifying the detected region of interest;
displaying an emphasis display for emphasizing the region of interest and a classification for the region of interest on a screen identical to a screen for displaying an observation target included in the medical image;
determining at least any of whether to change a display style of the emphasis display or whether to change a display style of the classification, and
reducing a degree of emphasis of the emphasis display in a case where the display style of the emphasis display is determined to change and reducing visual recognizability of the classification in a case where the display style of the classification is determined to be changed.

* * * * *